(12) United States Patent
Bakos et al.

(10) Patent No.: US 11,051,819 B2
(45) Date of Patent: Jul. 6, 2021

(54) LATCH TO PREVENT BACK-DRIVING OF CIRCULAR SURGICAL STAPLER

(71) Applicant: ETHICON LLC, Guaynabo, PR (US)

(72) Inventors: Gregory J. Bakos, Mason, OH (US); Michael A. Jacobs, Vilia Hills, KY (US); Michael J. Stokes, Cincinnati, OH (US); Gregory G. Scott, Cincinnati, OH (US); Disha V. Labhasetwar, Cincinnati, OH (US); Nicholas M. Morgan, West Chester, OH (US)

(73) Assignee: Cilag GmbH International, Zug (CH)

( * ) Notice: Subject to any disclaimer, the term of this patent is extended or adjusted under 35 U.S.C. 154(b) by 177 days.

(21) Appl. No.: 16/159,848

(22) Filed: Oct. 15, 2018

(65) Prior Publication Data
US 2020/0113565 A1   Apr. 16, 2020

(51) Int. Cl.
*A61B 17/115*   (2006.01)
*A61B 90/00*   (2016.01)
(Continued)

(52) U.S. Cl.
CPC .......... *A61B 17/1155* (2013.01); *A61B 90/08* (2016.02); *A61B 17/072* (2013.01);
(Continued)

(58) Field of Classification Search
CPC . A61B 17/068; A61B 17/1155; A61B 17/072; A61B 2017/00367;
(Continued)

(56) References Cited

U.S. PATENT DOCUMENTS

| 5,205,459 A | 4/1993 | Brinkerhoff et al. |
| 5,271,544 A | 12/1993 | Fox et al. |

(Continued)

FOREIGN PATENT DOCUMENTS

| EP | 3 108 825 A2 | 12/2016 |
| EP | 2100561 B1 | 8/2018 |

(Continued)

OTHER PUBLICATIONS

U.S. Appl. No. 16/159,851 entitled, "Dual Stage Closure System for Circular Surgical Stapler," filed Oct. 15, 2018.

(Continued)

*Primary Examiner* — Valentin Neacsu
(74) *Attorney, Agent, or Firm* — Frost Brown Todd LLC

(57) ABSTRACT

An apparatus includes a handle assembly having a body, a shaft assembly having an outer tubular member extending distally from the body, an end effector, an anvil, and a trocar latch assembly. The end effector includes a staple deck fixed relative to the outer tubular member, a staple driver that can actuate relative to the staple deck between an unfired position and a fired position, and a trocar that can actuate relative to the staple deck and the staple driver, the anvil can couple with trocar to move relative to the staple deck to define a gap distance. The trocar latch assembly includes a locking body that can actuate between an unlocked configuration and a locked configuration in response to the staple driver actuating between the unfired position and the fired position. The locking body can selective fix the trocar relative to the staple deck in the locked position.

15 Claims, 28 Drawing Sheets

(51) Int. Cl.
*A61B 17/00* (2006.01)
*A61B 17/072* (2006.01)

(52) U.S. Cl.
CPC ..... *A61B 90/03* (2016.02); *A61B 2017/00367* (2013.01); *A61B 2017/00407* (2013.01); *A61B 2017/00477* (2013.01); *A61B 2090/034* (2016.02); *A61B 2090/0811* (2016.02)

(58) Field of Classification Search
CPC ........... A61B 2017/00407; A61B 2017/00477; A61B 2090/0811; A61B 2090/034
USPC ..................... 227/175.2, 175.1, 175.3, 176.1
See application file for complete search history.

(56) References Cited

U.S. PATENT DOCUMENTS

| | | | |
|---|---|---|---|
| 5,275,322 A | 1/1994 | Brinkerhoff et al. | |
| 5,285,945 A | 2/1994 | Brinkerhoff et al. | |
| 5,292,053 A | 4/1994 | Bilotti et al. | |
| 5,333,773 A | 8/1994 | Main et al. | |
| 5,350,104 A | 9/1994 | Main et al. | |
| 5,533,661 A | 7/1996 | Main et al. | |
| 7,794,475 B2 | 9/2010 | Hess et al. | |
| 8,066,167 B2 * | 11/2011 | Measamer | A61B 90/06 227/175.2 |
| 8,910,847 B2 | 12/2014 | Nalagatla et al. | |
| 9,289,207 B2 | 3/2016 | Shelton, IV | |
| 9,463,022 B2 | 10/2016 | Swayze et al. | |
| 9,498,222 B2 | 11/2016 | Scheib et al. | |
| 9,532,783 B2 | 1/2017 | Swayze et al. | |
| 9,572,573 B2 | 2/2017 | Scheib et al. | |
| 9,597,081 B2 | 3/2017 | Swayze et al. | |
| 9,717,496 B2 * | 8/2017 | Mandakolathur Vasudevan | A61B 17/115 |
| 9,724,100 B2 | 8/2017 | Scheib et al. | |
| 9,936,949 B2 | 4/2018 | Measamer et al. | |
| 10,111,684 B2 * | 10/2018 | Williams | A61B 17/072 |
| 10,413,299 B2 * | 9/2019 | Milliman | A61B 17/068 |
| 10,478,189 B2 * | 11/2019 | Bear | H02J 7/00 |
| 10,524,797 B2 * | 1/2020 | Sgroi | A61B 17/34 |
| 10,702,302 B2 * | 7/2020 | Williams | A61B 17/34 |
| 10,772,627 B2 * | 9/2020 | Murugesan | A61B 17/1155 |
| 2010/0237132 A1 * | 9/2010 | Measamer | A61B 90/06 227/180.1 |
| 2014/0158747 A1 | 6/2014 | Measamer et al. | |
| 2016/0066906 A1 * | 3/2016 | Mandakolathur Vasudevan | A61B 17/068 227/175.2 |
| 2016/0374665 A1 * | 12/2016 | DiNardo | A61B 17/068 227/175.2 |
| 2016/0374670 A1 * | 12/2016 | Fox | A61B 17/072 227/175.1 |
| 2016/0374672 A1 * | 12/2016 | Bear | H02J 7/00 606/219 |
| 2016/0374684 A1 | 12/2016 | DiNardo et al. | |
| 2017/0086879 A1 * | 3/2017 | Williams | A61B 17/1155 |
| 2017/0150968 A1 * | 6/2017 | Milliman | A61B 17/1155 |
| 2017/0196566 A1 * | 7/2017 | Sgroi | A61B 17/34 |
| 2017/0215883 A1 * | 8/2017 | Miller | A61B 17/115 |
| 2017/0333077 A1 * | 11/2017 | Williams | A61B 17/34 |
| 2017/0348002 A1 * | 12/2017 | Murugesan | A61B 17/07207 |
| 2018/0021041 A1 * | 1/2018 | Zhang | A61B 17/07207 227/175.2 |

FOREIGN PATENT DOCUMENTS

| | | |
|---|---|---|
| WO | WO 2016/090600 A1 | 6/2016 |
| WO | WO 2016/127434 A1 | 8/2016 |

OTHER PUBLICATIONS

U.S. Appl. No. 16/159,854 entitled, "Dual Lever to Reduce Force to Fire in Circular Surgical Stapler," filed Oct. 15, 2018.
European Search Report, Partial, and Provisional Written Opinion dated Feb. 14, 2020 for Application No. EP 19203085.6, 12 pgs.
European Search Report, Extended, and Written Opinion dated Jun. 26, 2020 for Application No. EP 19203085.6, 11 pgs.
International Search Report and Written Opinion dated Mar. 9, 2020 for Application No. PCT/IB2019/058695, 19 pgs.
European Examination Report dated Feb. 16, 2021 for Application No. EP 19203085.6, 6 pgs.

* cited by examiner

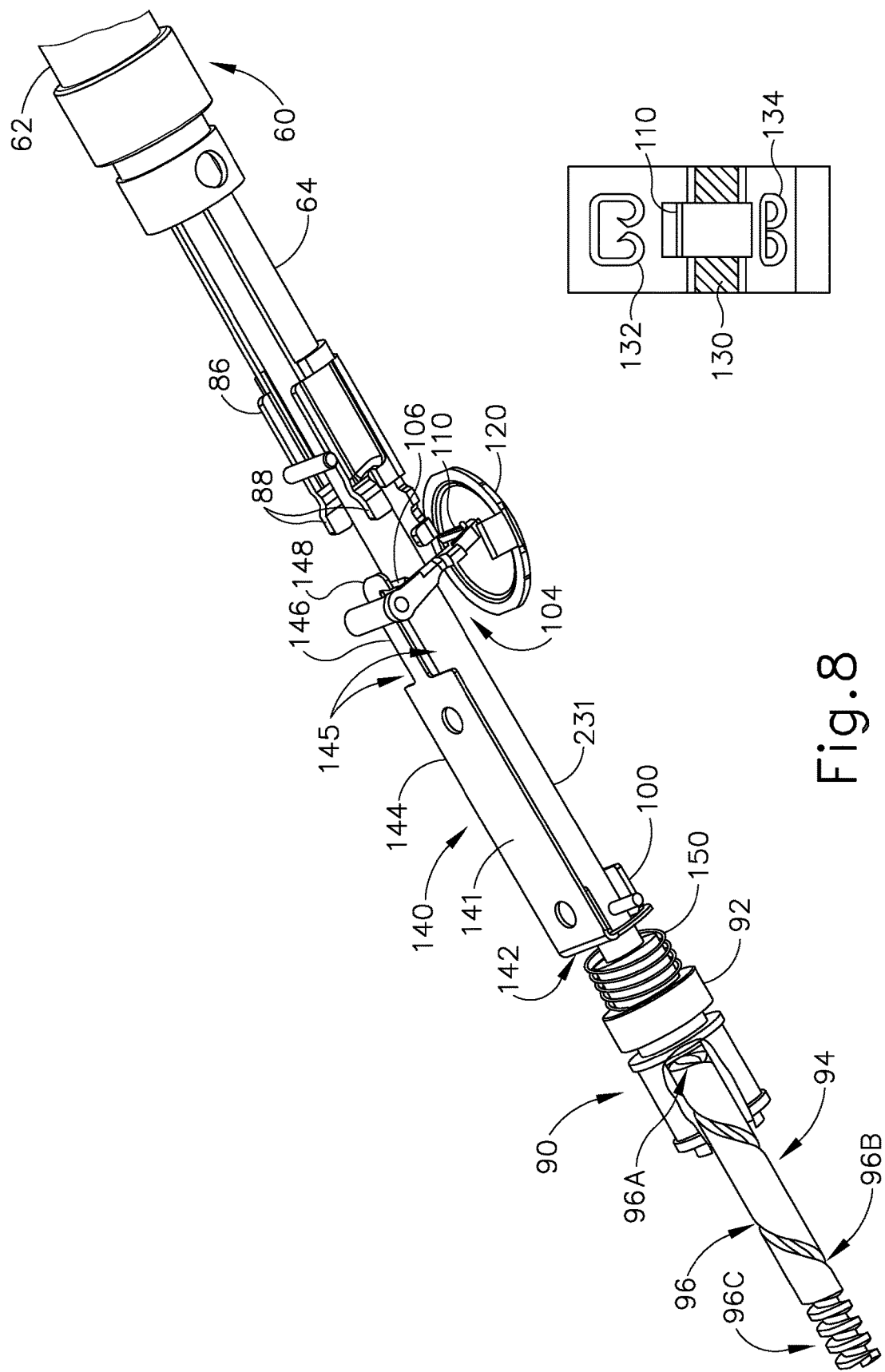

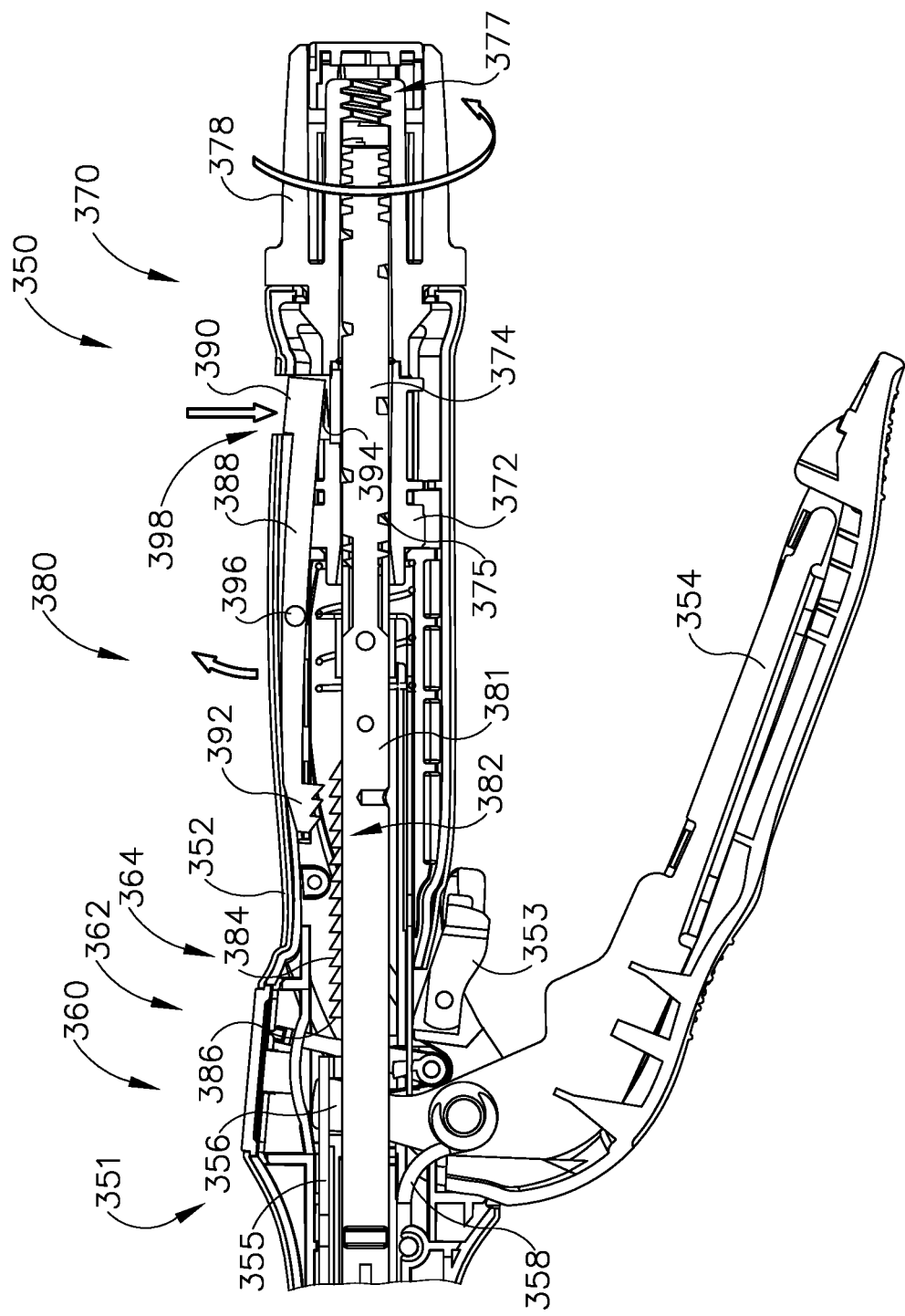

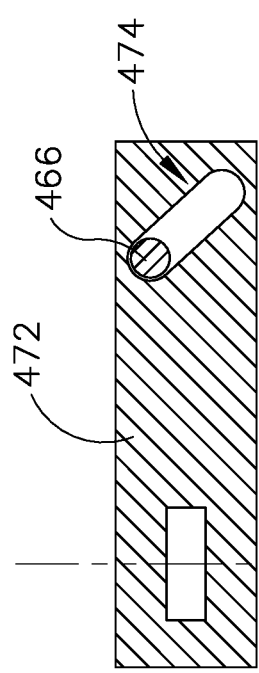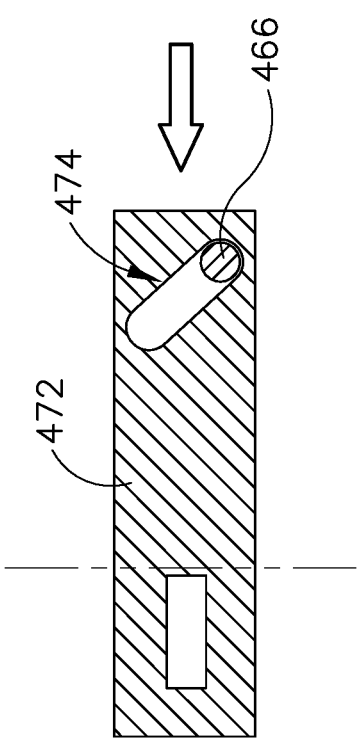

LATCH TO PREVENT BACK-DRIVING OF CIRCULAR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8 depicts an enlarged partial perspective view of an exemplary indicator assembly of the surgical instrument of FIG. 1, showing an indicator window and indicator lever;

FIG. 9 depicts a diagrammatic view of the indicator window of FIG. 10, showing an exemplary indicator bar and exemplary corresponding staple representations;

FIG. 14C depicts a cross-sectional side view of the actuator handle assembly of FIG. 14A, where the trocar actuator is in a position associated with the anvil in the second open position shown in FIG. 10D, where the latch assembly of FIG. 14A is in an unlocked position;

FIG. 17A depicts a cross-sectional view taken along line 17A-17A of FIG. 16A, where a camming feature is in a proximal position;

FIG. 17B depicts a cross-sectional view taken along line 17B-17B of FIG. 16B, where the camming feature of FIG. 17A is in a distal position;

Figure 1:
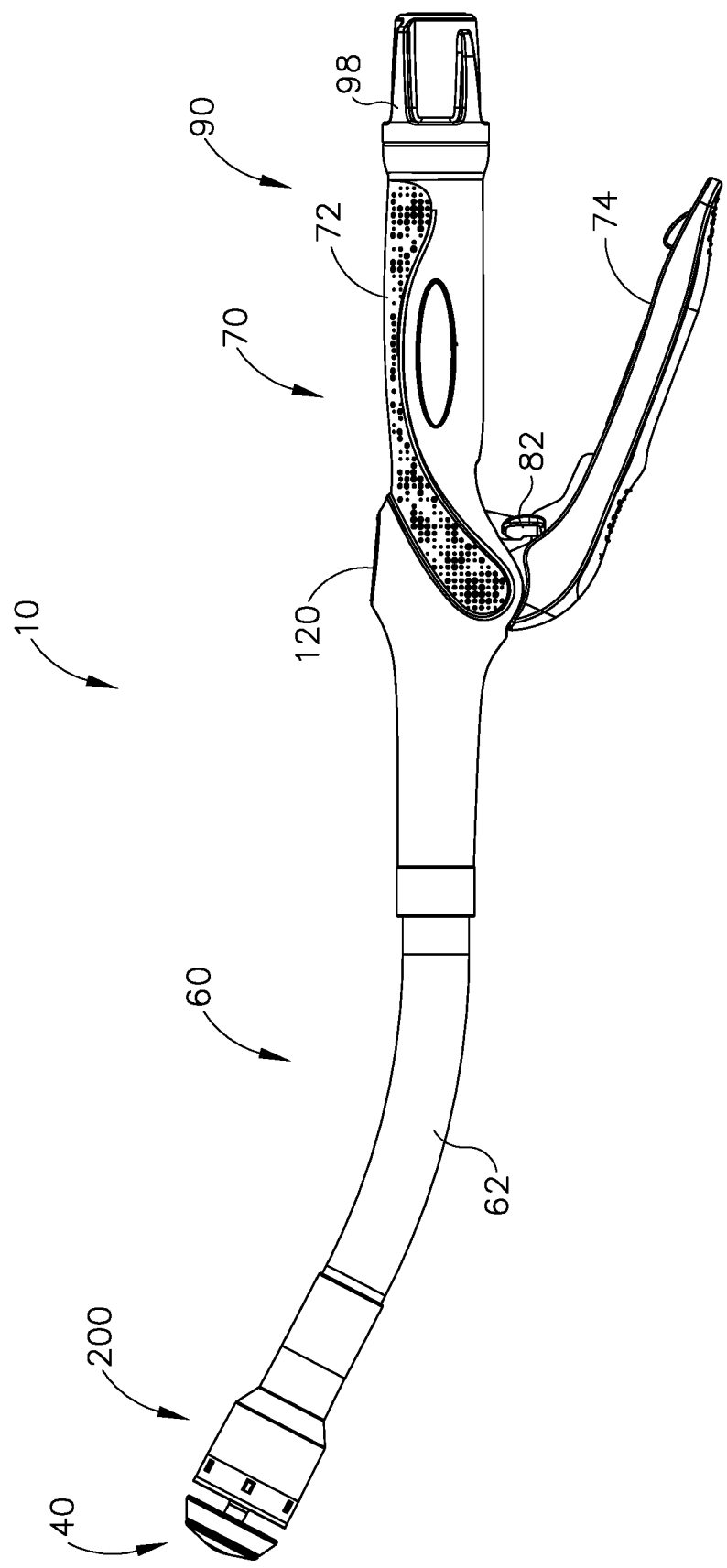
FIG. 1 depicts a side elevation view of an exemplary circular stapling surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-12B depict an exemplary circular surgical stapling instrument (10) having a stapling head assembly (200), a shaft assembly (60), and an actuator handle assembly (70), each of which will be described in more detail below. Shaft assembly (60) extends distally from actuator handle assembly (70), while stapling head assembly (200) is coupled to a distal end of shaft assembly (60). In brief, actuator handle assembly (70) is operable to actuate a staple driver member (250) of stapling head assembly (200) to drive a plurality of staples (66) out of stapling head assembly (200). Staples (66) are bent to form completed staples by an anvil (40) that is selectively attached at the distal end of instrument (10). Accordingly, tissue (2), as shown in FIGS. 10A-10E, may be stapled utilizing instrument (10).

In the present example, instrument (10) comprises a closure system and a firing system. As will be described in greater detail below, the closure system and anvil (40) are operable to clamp tissue between anvil (40) and stapling head assembly (200). As will also be described in greater detail below, the firing system and anvil (40) are operable to cut and staple tissue clamped between anvil (40) and stapling head assembly (200).

The closure system comprises a trocar (230), a trocar actuator (231), a connecting band portion (235), and an adjustment knob (98). Trocar actuator (231) is coupled to trocar (230) via connecting band portion (235). Anvil (40) may be selectively coupled to a distal end of trocar (230). Adjustment knob (98) is operable to longitudinally translate trocar (230) relative to stapling head assembly (200), thereby translating anvil (40) when anvil (40) is suitably coupled to trocar (230), and further clamping tissue between anvil (40) and stapling head assembly (200) as will be described in greater detail below.

The firing system comprises a trigger (74), a trigger actuation assembly (84), a driver actuator (64), and a staple driver member (250). Staple driver member (250) includes a knife member (240) configured to sever tissue when staple driver member (250) is actuated longitudinally. In addition, staples (66) are positioned distal to a plurality of staple drivers of staple driver member (250) such that staple driver member (250) also drives staples (66) distally when staple driver member (250) is actuated longitudinally. Thus, when trigger (74) is actuated and trigger actuation assembly (84) actuates staple driver member (250) via driver actuator (64), knife member (240) and staple drivers (252) substantially simultaneously sever tissue (2) and drive staples (66) distally relative to stapling head assembly (200) into tissue. The components and functionalities of the closure system and firing system will now be described in greater detail.

A. Exemplary Anvil

In the following discussion of anvil (40), the terms "distal" and "proximal" (and variations thereof) will be used with reference to the orientation of anvil (40) when anvil (40) is suitably coupled with trocar (230). Thus, proximal features of anvil (40) will be closer to the operator of instrument (10); while distal features of anvil (40) will be further from the operator of instrument (10).

Figure 3:
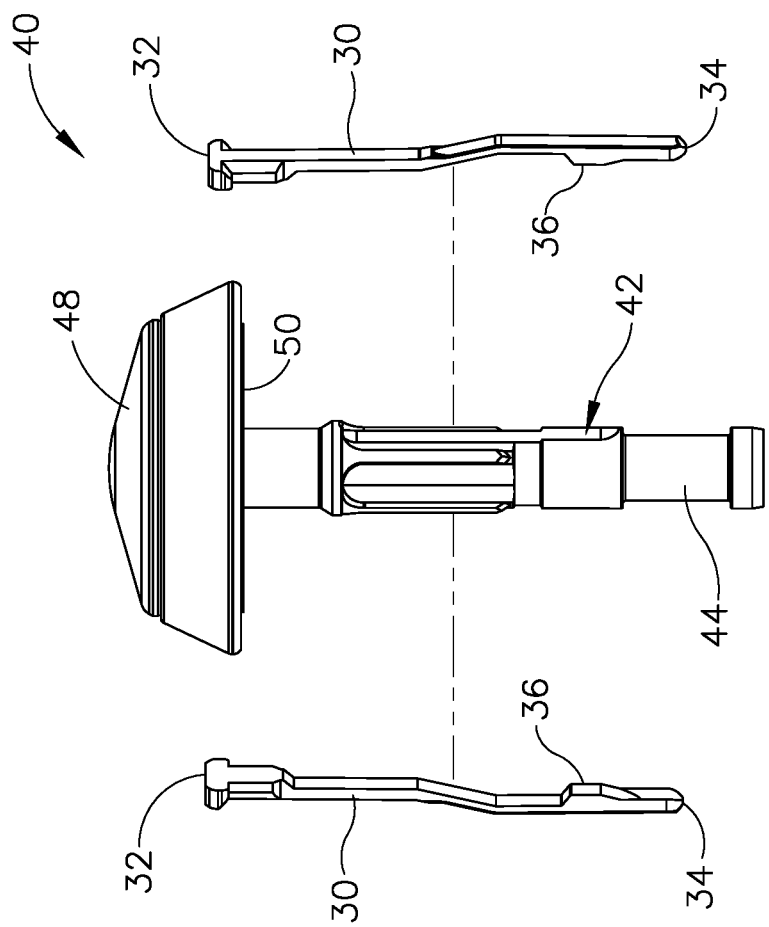
FIG. 3 depicts an exploded side elevational view of the anvil of FIG. 2.
Figure 2:
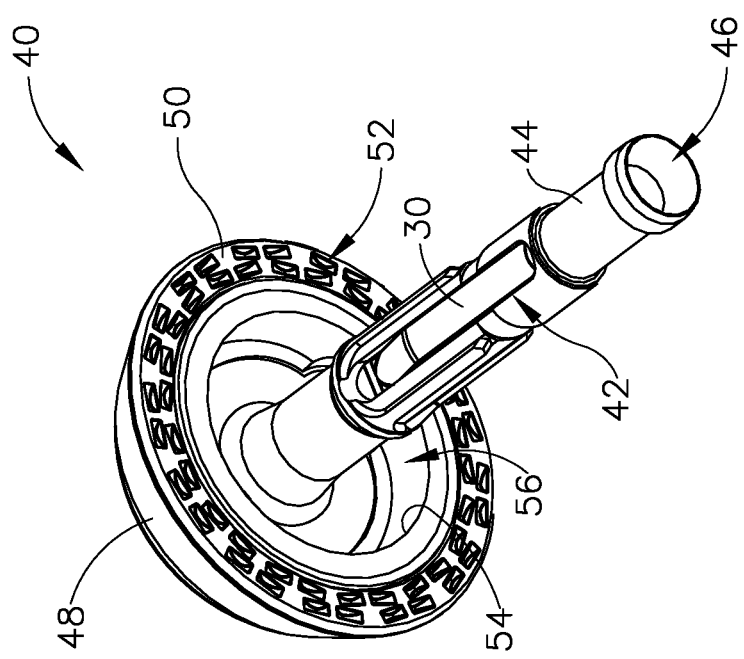
FIG. 2 depicts a perspective view of an exemplary anvil of the surgical instrument of FIG. 1.

As best seen in FIGS. 2-3, anvil (40) of the present example comprises a head (48) and a proximal shaft (44). As mentioned above and as will be described in greater detail below, anvil (40) of the present example may selectively couple to trocar (230) such that when coupled, movement of trocar (230) relative to stapling head assembly (200) also moves anvil (40) relative to stapling head assembly (200).

Head (48) includes a proximal surface (50) that defines a plurality of staple forming pockets (52). Staple forming pockets (52) are arranged in two concentric annular arrays. In some other versions, staple forming pockets (52) are arranged in three or more concentric annular arrays. Staple forming pockets (52) are configured to deform staples as the staples are driven into staple forming pockets (52). Accordingly, when anvil (40) is in the closed position and staples (66) are driven out of stapling head assembly (200) into staple forming pockets (52), each staple forming pocket (52) may deform a generally "U" shaped staple (66) into a "B" shape as is known in the art. As best seen in FIG. 2, proximal surface (50) terminates at an inner edge (54), which defines an outer boundary of an annular recess (56) surrounding proximal shaft (44).

Proximal shaft (44) defines a bore (46) and includes a pair of pivoting latch members (30) positioned in bore (46). As best seen in FIG. 3, each latch member (30) includes a "T" shaped distal end (32), a rounded proximal end (34), and a latch shelf (36) located distal to proximal end (34). "T" shaped distal ends (32) secure latch members (30) within bore (46). Latch members (30) are positioned within bore (46) such that proximal ends (34) are positioned at the proximal ends of lateral openings (42), which are formed through the sidewall of proximal shaft (44). Lateral openings (42) thus provide clearance for proximal ends (34) and latch shelves (36) to deflect radially outwardly from the longitudinal axis defined by proximal shaft (44). However, latch members (30) are configured to resiliently bias proximal ends (34) and latch shelves (36) radially inwardly toward the longitudinal axis defined by proximal shaft (44). Latch members (30) thus act as retaining clip to allow anvil (40) to be selectively secured to trocar (230) of stapling head assembly (200). It should be understood, however, that latch members (30) are merely optional. Anvil (40) may be removably secured to a trocar (230) using any other suitable components, features, or techniques.

In addition to or in lieu of the foregoing, anvil (40) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or U.S. Pub. No. 2016/0374684, the disclosures of which are incorporated by reference herein. Still other suitable configurations will be apparent to one of ordinary skill in the art in view of the teachings herein.

B. Exemplary Stapling Head Assembly

Figure 4:
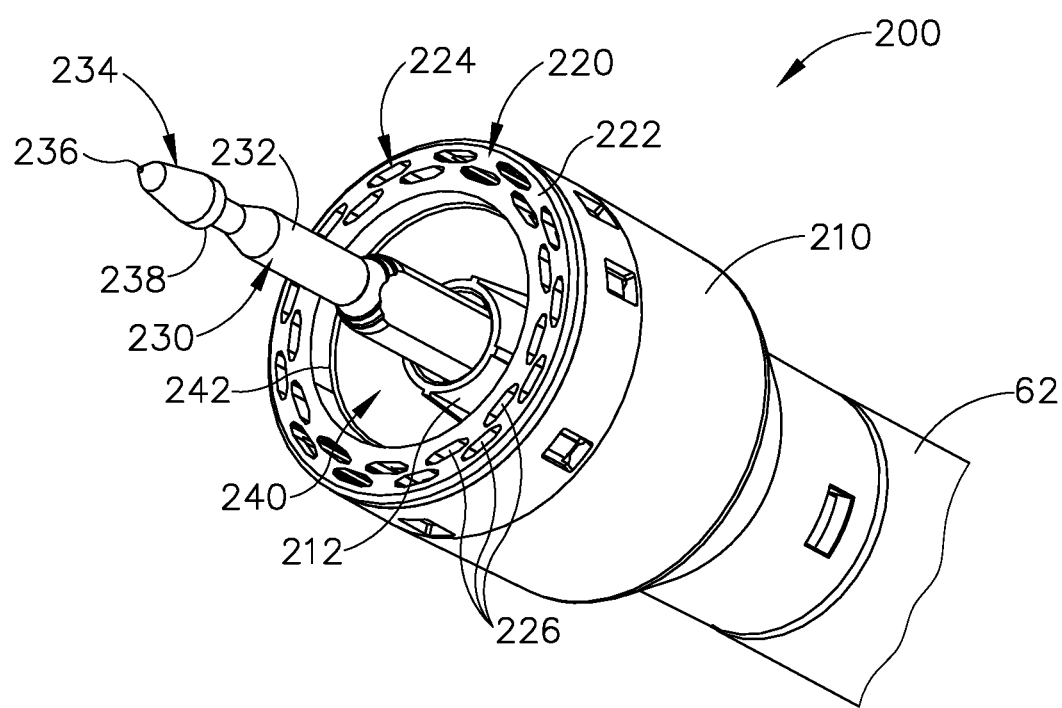
FIG. 4 depicts a perspective view of a stapling head assembly of the surgical instrument of FIG. 1.
Figure 5:
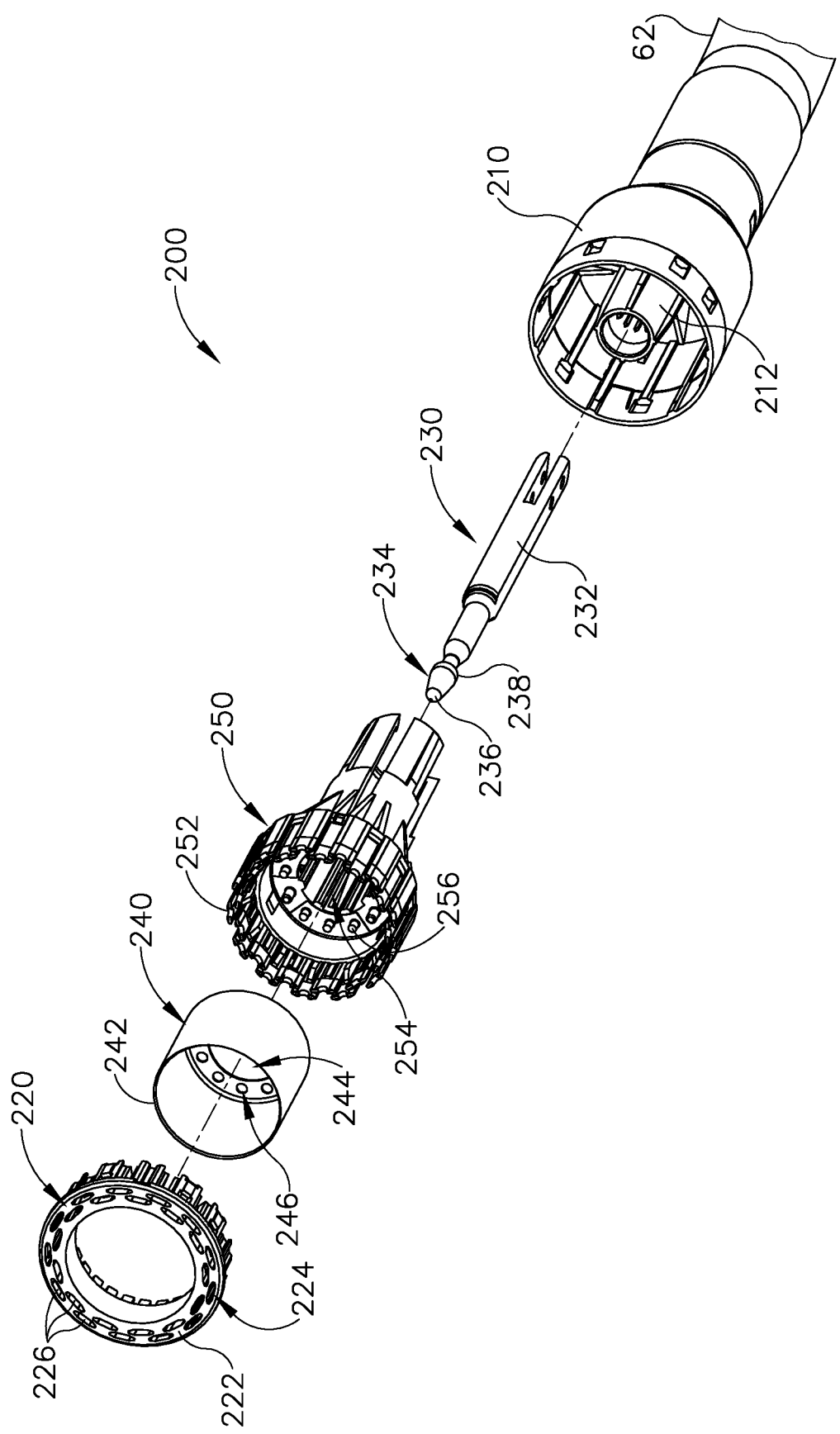
FIG. 5 depicts an exploded perspective view of the stapling head assembly of FIG. 5.

As best seen in FIGS. 4-5, stapling head assembly (200) of the present example is coupled to a distal end of shaft assembly (60) and comprises a tubular casing (210) housing a slidable staple driver member (250). A cylindraceous inner core member (212) extends distally within tubular casing (210). Tubular casing (210) is fixedly secured to an outer tubular member (62) of shaft assembly (60), such that tubular casing (210) serves as a mechanical ground for stapling head assembly (200).

Trocar (230) is positioned coaxially within inner core member (212) of tubular casing (210). As mentioned above and as will be described in greater detail below, trocar (230) is operable to translate distally and proximally relative to tubular casing (210) in response to rotation of adjustment knob (98) relative to body (72) of handle assembly (70). Trocar (230) comprises a shaft (232) and a head (234). Head (234) includes a pointed tip (236) and an inwardly extending proximal surface (238). Shaft (232) thus provides a reduced outer diameter just proximal to head (234), with surface (238) providing a transition between that reduced outer diameter of shaft (232) and the outer diameter of head (234). While tip (236) is pointed in the present example, tip (236) is not sharp. Tip (236) will thus not easily cause trauma to tissue due to inadvertent contact with tissue. Head (234) and the distal portion of shaft (232) are configured for insertion in bore (46) of anvil (40). Proximal surface (238) and latch shelves (36) have complementary positions and configurations such that latch shelves (36) engage proximal surface (238) when proximal shaft (44) of anvil (40) is fully seated on trocar (230). Anvil (40) may thus secure to trocar (230) through a snap fitting between latch members (30) and head (234). In addition, or in the alternative, trocar (230) may include a magnetic portion (not shown) which may attract anvil (40) towards trocar (230). Still further configurations and arrangements for anvil (40) and trocar (230) will be apparent to one of ordinary skill in the art in view of the teachings herein.

Figure 10A:
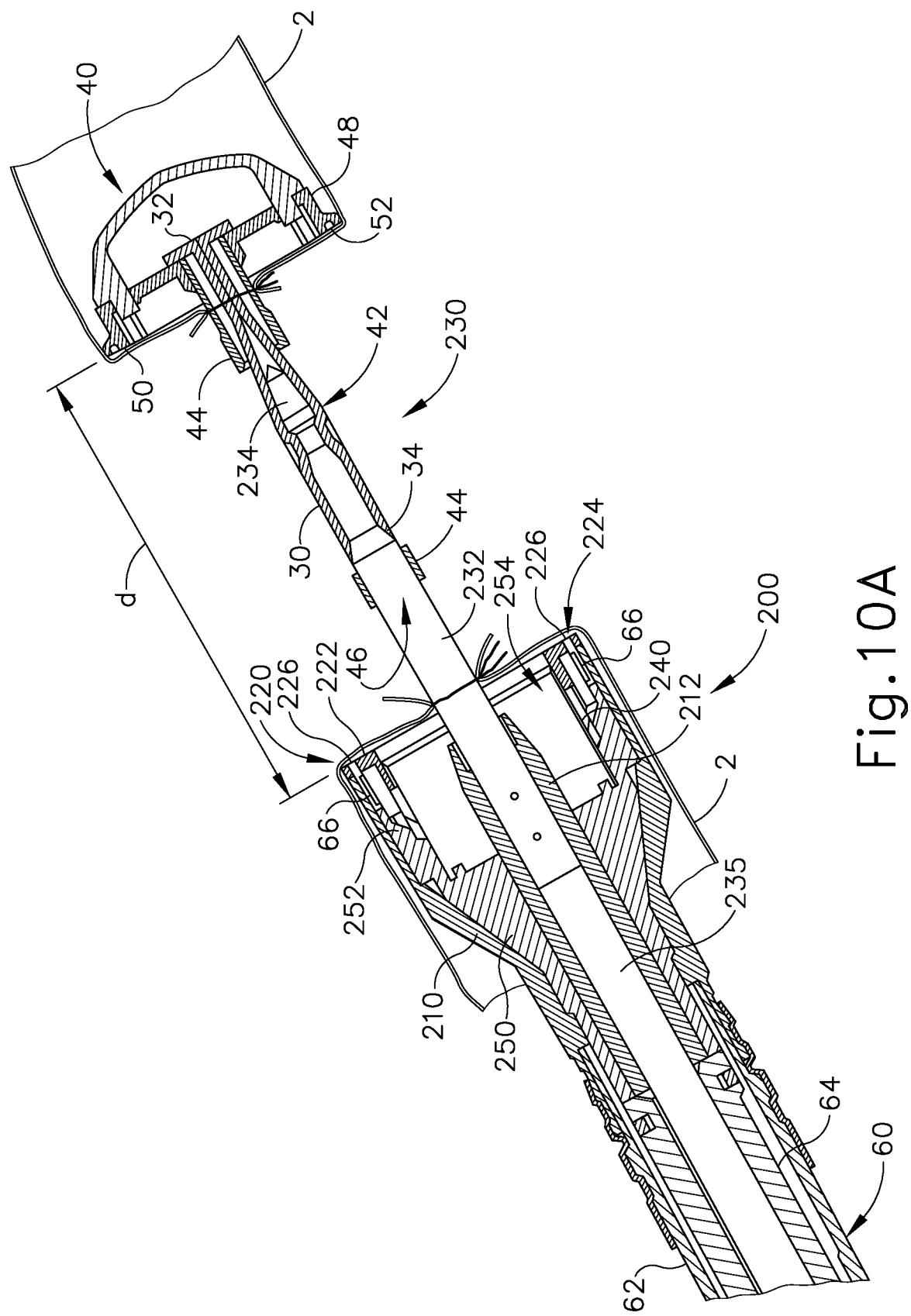
FIG. 10A depicts an enlarged longitudinal cross-section view of the stapling head assembly of FIG. 5, showing the anvil of FIG. 2 in a first open position, where the anvil is within a first tubular portion of tissue and the stapling head assembly is within a second tubular portion of tissue.
Figure 10B:
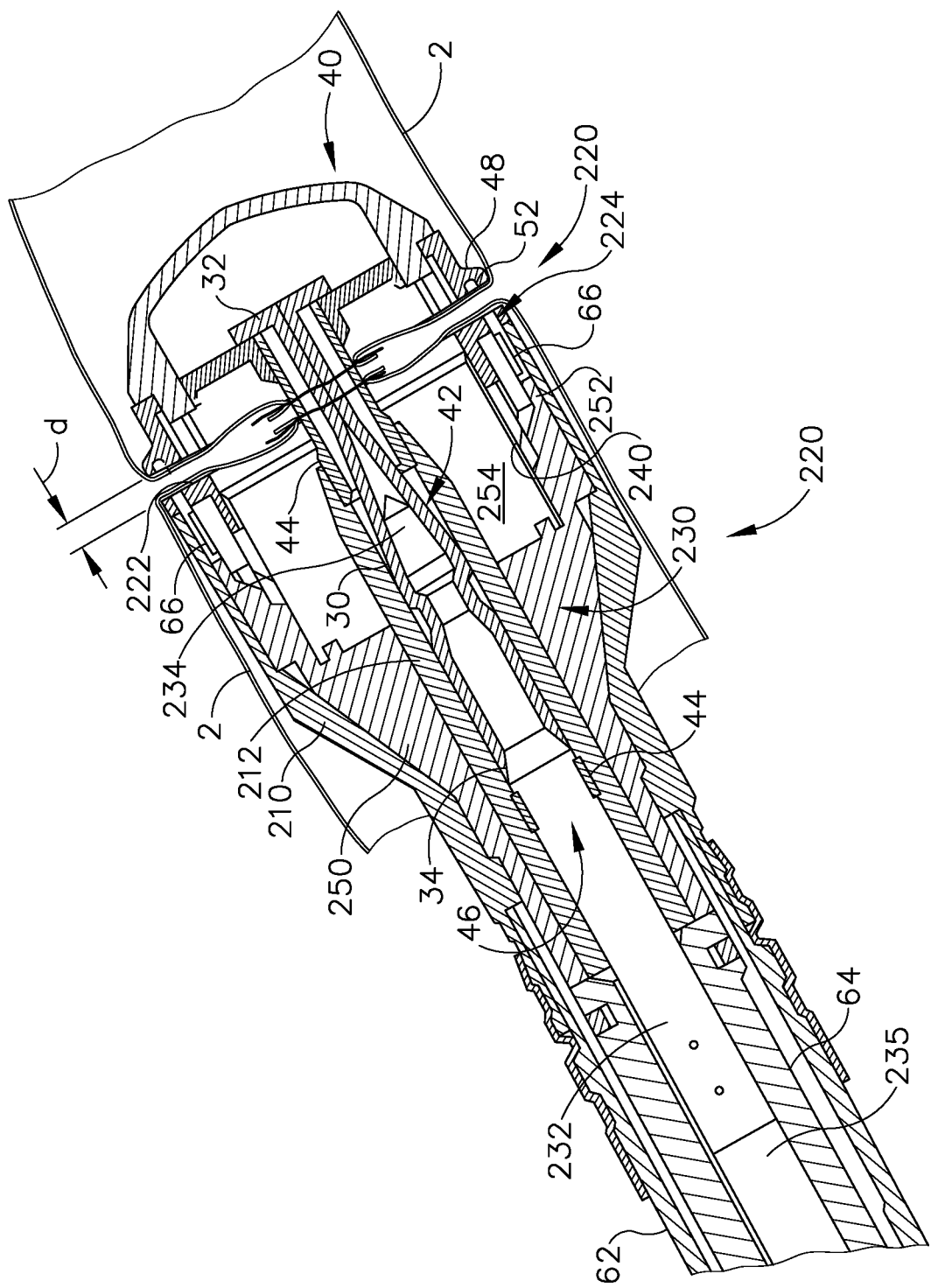
FIG. 10B depicts an enlarged longitudinal cross-sectional view of the stapling head assembly of FIG. 5, showing the anvil of FIG. 2 in a closed position, where the anvil is within the first tubular portion of tissue and the stapling head assembly is within the second tubular portion of tissue.

Staple driver member (250) is operable to actuate longitudinally within tubular casing (210) in response to rotation of trigger (74) of actuator handle assembly (70) as will be described in greater detail below. Staple driver member (250) includes two distally presented concentric annular arrays of staple drivers (252). Staple drivers (252) are arranged to correspond with the arrangement of staple forming pockets (52) described above. As best seen in FIGS. 10A-10B, each staple driver (252) is located underneath a corresponding staple (66). The arrangement of staple drivers (252) may be modified just like the arrangement of staple forming pockets (52) as described above. Staple driver member (250) also defines a bore (254) that is configured to coaxially receive core member (212) of tubular casing (210). An annular array of studs (256) project distally from a distally presented surface surrounding bore (254).

A cylindraceous knife member (240) is coaxially positioned within staple driver member (250). Knife member (240) includes a distally presented, sharp circular cutting edge (242). Knife member (240) is sized such that knife member (240) defines an outer diameter that is smaller than the diameter defined by the inner annular array of staple drivers (252). Knife member (240) also defines an opening that is configured to coaxially receive core member (212) of tubular casing (210). An annular array of openings (246) formed in knife member (240) is configured to complement the annular array of studs (256) of staple driver member (250), such that knife member (240) is fixedly secured to staple driver member (250) via studs (256) and openings (346). Therefore, when stapling driver member (250) is actuated relative to tubular casing (210), so is knife member (240). Other suitable structural relationships between knife member (240) and stapler driver member (250) will be apparent to those of ordinary skill in the art in view of the teachings herein.

A deck member (220) is fixedly secured to tubular casing (210). Deck member (220) includes a distally presented deck surface (222) defining two concentric annular arrays of staple openings (224), where each staple opening (224) has its own staple pocket (226) housing a staple (66). Staple openings (224) and staple pockets (226) are arranged to correspond with the arrangement of staple drivers (252) and staple forming pockets (52) described above. Accordingly, when staple driver member (250) is actuated distally relative to tubular casing (210) in response to rotation of trigger (74), each staple driver (252) drives a corresponding staple (66) out of its staple pocket (226) and through a corresponding staple opening (224) of deck member (220). When anvil (40) is in the closed position, staples (66) are driven into a corresponding staple forming pockets (52) to bend legs (68) of the staples (66), thereby stapling the material located between anvil (40) and stapling head assembly (200).

The arrangement of staple openings (224) may be modified just like the arrangement of staple forming pockets (52) as described above. It should also be understood that various structures and techniques may be used to contain staples (66) within stapling head assembly (200) before stapling head assembly (200) is actuated. Such structures and techniques that are used to contain staples within stapling head assembly (200) may prevent the staples from inadvertently falling out through staple openings (224) before stapling head assembly (200) is actuated. Various suitable forms that such structures and techniques may take will be apparent to those of ordinary skill in the art in view of the teachings herein.

As best seen in FIG. 5, deck member (220) defines an inner diameter that is just slightly larger than the outer diameter defined by knife member (240). Deck member (220) is thus configured to allow knife member (240) to translate distally to a point where cutting edge (242) is distal to deck surface (222).

In addition to or in lieu of the foregoing, stapling head assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or U.S. Pub. No. 2016/0374684, the disclosures of which are incorporated by reference herein. Still other suitable configurations will be apparent to one of ordinary skill in the art in view of the teachings herein.

C. Exemplary Shaft Assembly

Stapling head assembly (200) and trocar (230) are positioned at a distal end of shaft assembly (60), as shown in FIGS. 10A-10D. Shaft assembly (60) of the present example comprises an outer tubular member (62), a driver actuator (64), and connecting band portion (235). Outer tubular member (62) is coupled to tubular casing (210) of stapling head assembly (200) and to a body (72) of actuator handle assembly (70), thereby providing a mechanical ground for the actuating components therein. As seen in FIGS. 7A-7B, the proximal end of driver actuator (64) is coupled to a trigger actuation assembly (84) of actuator handle assembly (70), as described below. The distal end of driver actuator (64) is coupled to staple driver member (250) such that the rotation of trigger (74) longitudinally actuates staple driver member (250). As shown in FIGS. 10A-10D, driver actuator (64) comprises a tubular member having an open longitudinal axis such that trocar actuator (231) and connecting band portion (235), which are coupled to trocar (230), may actuate longitudinally within and relative to driver actuator (64). Other components may be disposed within driver actuator (64) as will be apparent to one of ordinary skill in the art in view of the teachings herein.

In the present example, shaft assembly (60) extends distally from actuator handle assembly (70) with a preformed bend. In some versions, the preformed bend is configured to facilitate positioning of stapling head assembly (200) within a patient's colon. Various suitable bend angles or radii that may be used will be apparent to those of ordinary skill in the art in view of the teachings herein. As mentioned above, actuator (231) is coupled with trocar (230) via flexible band portion (235). Flexible band portion (235) extends from a distal end of actuator (231), located proximal to the preformed bend, to couple with trocar (230), located distal to the preformed bend. Flexible band portion (235) may be dimensioned to flex during translation along the longitudinal profile of the preformed bend of shaft assembly (60). In such cases, trocar actuator (231) may be slidably housed within actuator handle assembly (70), while trocar (230) is slidably housed within tubular casing (210). Flexible band portion (235) may be connected to both trocar (230) and actuator (231) via pins or any other suitable means as would be apparent to one having ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or 9,936,949, the disclosures of which are incorporated by reference herein; and/or in accordance with other configurations as will be apparent to one of ordinary skill in the art in view of the teachings herein.

D. Exemplary Actuator Handle Assembly

Figure 12A:
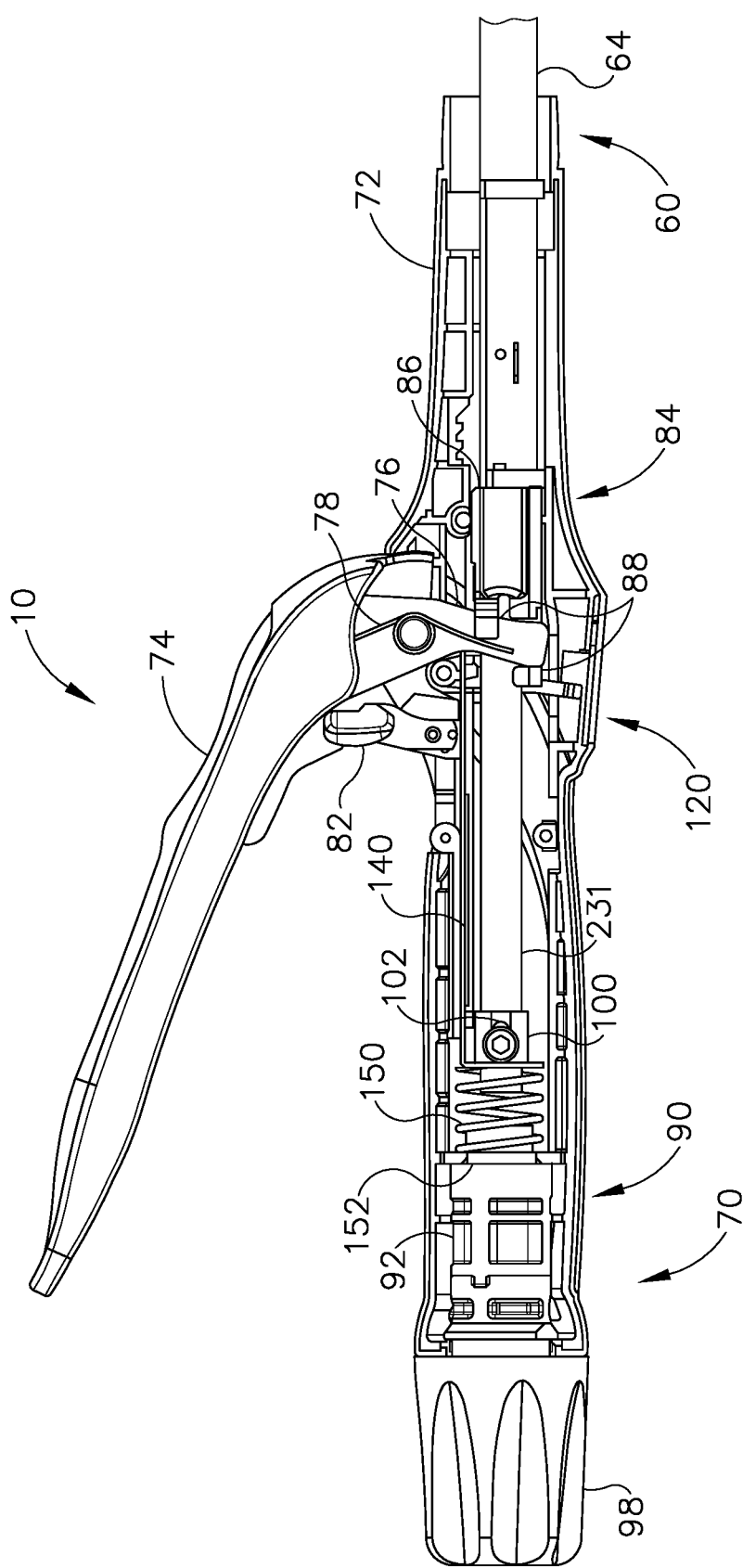
FIG. 12A depicts an enlarged side elevation view of an exemplary actuator handle assembly of the surgical instrument of FIG. 1 with a portion of the body removed, showing a trigger in an unfired position and a lockout feature in a locked position.

Referring now to FIGS. 6-8 and 12A-12B, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 12A) to a fired position (shown in FIG. 12B) actuates driver actuator (64) described above. A spring (78) is coupled to body (72) and trigger (74) to bias trigger (74) towards the unfired position. Lockout feature (82) is a pivotable member that is coupled to body (72). In a first, locked position, as shown in FIG. 12A, lockout feature (82) is pivoted upwards and away from body (72) such that lockout feature (82) engages trigger (74) and mechanically resists actuation of trigger (74) by a user. In a second, unlocked position, such as that shown in FIGS. 1 and 12B, lockout feature (82) is pivoted downward such that trigger (74) may be actuated by the user. Accordingly, with lockout feature (82) in the second position, trigger (74) can engage trigger actuation assembly (84) to fire instrument (10).

Figure 12B:
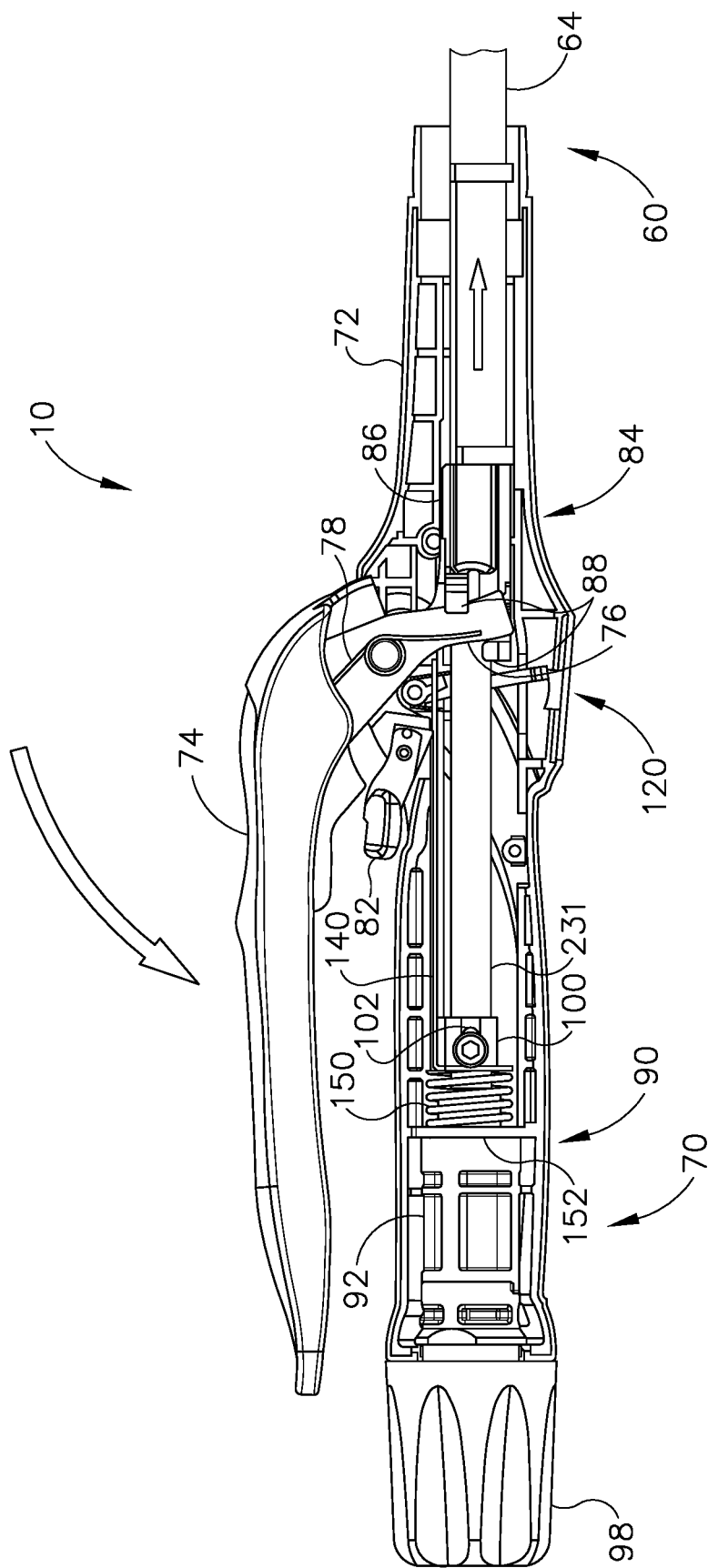
FIG. 12B depicts an enlarged side elevation view of the actuator handle assembly of FIG. 12A, showing the trigger in a fired position and the lockout feature in an unlocked position.

As shown in FIGS. 12A-12B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or 9,936,949 the disclosures of which are incorporated by reference herein; and/or in accordance with other configurations as will be apparent to one of ordinary skill in the art in view of the teachings herein.

Figure 6:
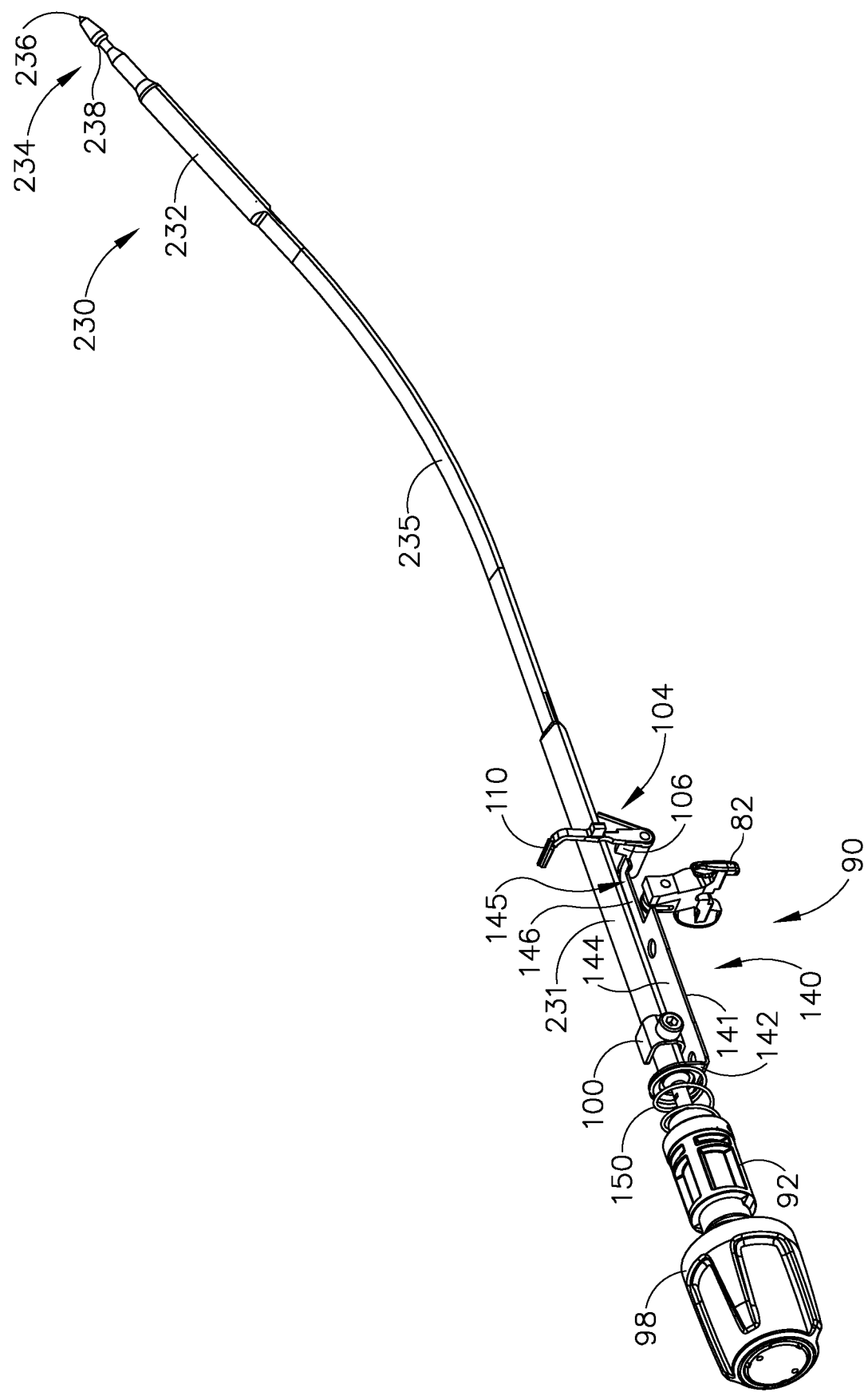
FIG. 6 depicts a perspective view of an exemplary closure system of the surgical instrument of FIG. 1.
Figure 7:
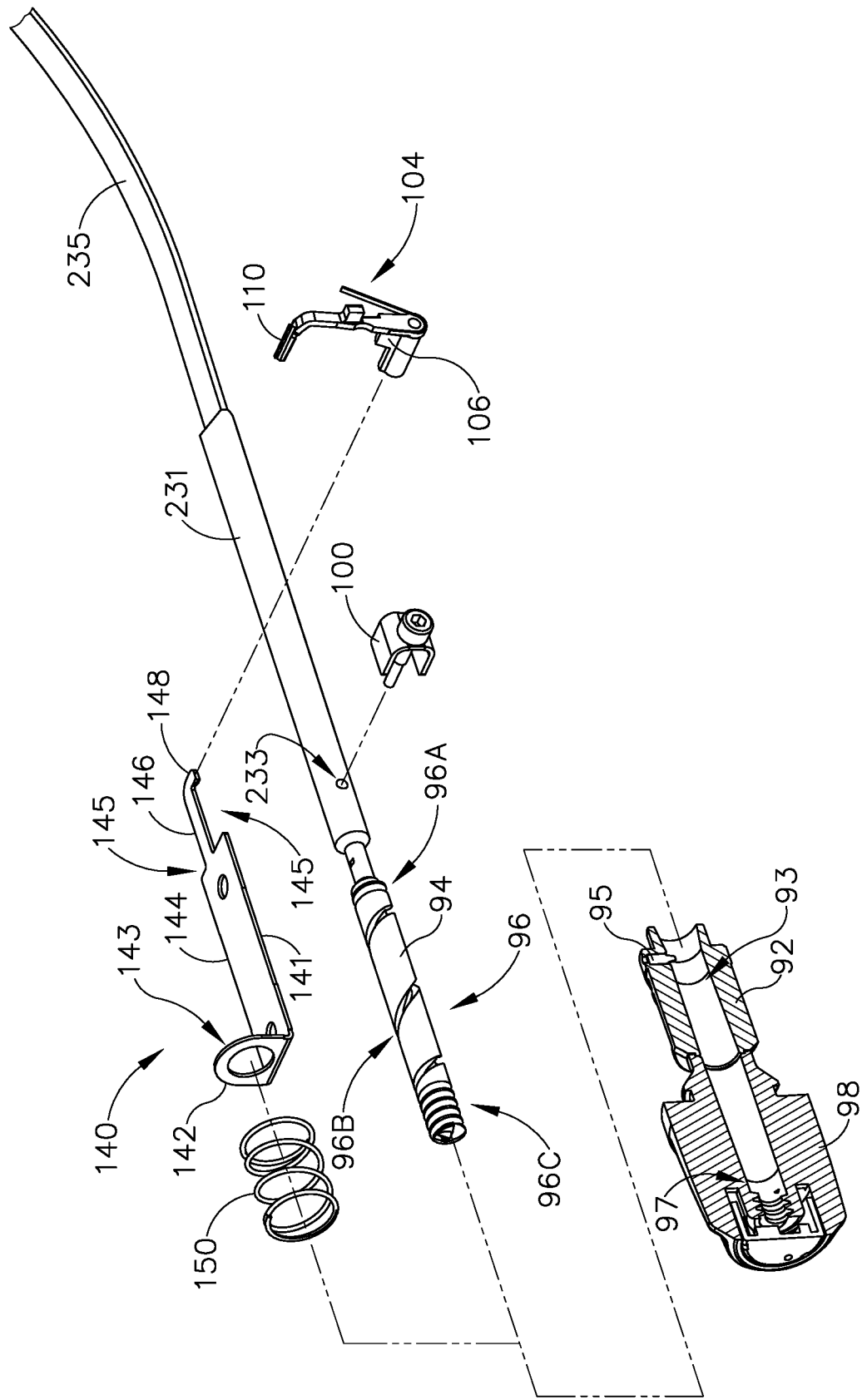
FIG. 7 depicts an exploded perspective view of the closure system of FIG. 1.

Body (72) also houses trocar actuation assembly (90) configured to actuate trocar (230) longitudinally in response to rotation of adjustment knob (98). As best shown in FIGS. 6-8, trocar actuation assembly (90) of the present example comprises adjustment knob (98), a grooved shank (94), and a sleeve (92). Grooved shank (94) is slidably housed within a channel (93) defined by both adjustment knob (98) and sleeve (92). Grooved shank (94) of the present example is located at a proximal end of trocar actuator (231). In other versions, grooved shank (94) and trocar actuator (231) may alternatively be separate components that engage to transmit longitudinal movement. While grooved shank (94) is configured to translate within body (72), grooved shank (94) does not rotate within body (72). Adjustment knob (98) is rotatably supported by the proximal end of body (72) and is operable to rotate sleeve (92), which is engaged with grooved shank (94) via an internal tab (95). Adjustment knob (98) also defines internal threading (97) as will be described in greater detail below. Grooved shank (94) of the present example comprises a continuous groove (96) formed in the outer surface of grooved shank (94). Accordingly, when adjustment knob (98) is rotated, internal tab (95) of sleeve (92) rides within groove (96) and grooved shank (94) is longitudinally actuated relative to sleeve (92). Since grooved shank (94) is located at the proximal end of trocar actuator (231), rotating adjustment knob (98) in a first direction advances trocar actuator (231) distally relative to actuator handle assembly (70). When trocar (230) is coupled with anvil (40), anvil (40) also advances distally relative to stapling head assembly (200) thereby increasing the distance between proximal surface (50) of the anvil (40) and distally presented deck surface (222) of deck member (220), otherwise known as a gap distance d. By rotating adjustment knob (98) in the opposite direction, trocar actuator (231) is actuated proximally relative to actuator handle assembly (70) to reduce the gap distance d between anvil (40) and stapling head assembly (200) when trocar (230) is coupled with anvil (40). Thus, trocar actuation assembly (90) is operable to actuate trocar (230) in response to rotating adjustment knob (98). Other suitable configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIGS. 7-8, distal portion (96A) comprises a fine pitch or a high number of grooves over a short axial length of grooved shank (94). Middle portion (96B) comprises a section with comparably coarser pitch or fewer grooves per axial length such that relatively few rotations are required for internal tab (95) of sleeve (92) to traverse along axial distance. When anvil (40) is in an initial, distal position in relation to stapling head assembly (200) (as shown in FIG. 10A) the internal tab (95) of sleeve (92) is positioned in middle portion (96B). Accordingly, the gap distance d may be quickly reduced through relatively few rotations of adjustment knob (98) while the internal tab (95) of sleeve (92) traverses middle portion (96B). Proximal portion (96C) of the present example is substantially like distal portion (96A) and comprises a fine pitch or a high number of grooves over a short axial distance of grooved shank (94) such that many rotations are required to traverse the short axial distance. Proximal portion (96C) of the present example is engaged by the internal threading (97) defined by knob (98) when anvil (40) is substantially near to stapling head assembly (200) (as shown in FIG. 10B), such that indicator bar (110) moves within indicator window (120) along scale (130) to indicate that the anvil gap is within a desired operating range, as will be described in more detail below. Accordingly, when grooved shank (94) reaches a proximal position where the proximal portion (96C) of groove (96) engages internal threading (97) of knob (98), each rotation of adjustment knob (98) may reduce the gap distance d by a relatively small amount to provide for fine tuning. Internal tab (95) of sleeve (92) may be disengaged from groove (96) when proximal portion (96C) is engaged with internal threading (97) of knob (98).

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or 9,936,949 the disclosures of which are incorporated by reference herein; and/or in accordance with other configurations as will be apparent to one of ordinary skill in the art in view of the teachings herein.

As noted above, gap distance d corresponds to the distance between anvil (40) and stapling head assembly (200). When instrument (10) is inserted into a patient, this gap distance d may not be easily viewable. Accordingly, a moveable indicator bar (110), shown in FIGS. 8-9, is provided to be visible through an indicator window (120) positioned opposite to trigger (74). As will be described in greater detail below, indicator bar (110) is operable to move in response to rotation of adjustment knob (98) such that the position of indicator bar (110) is representative of the gap distance d. As shown in FIG. 9, indicator window (120) further comprises a scale (130) which indicates that the anvil gap is within a desired operating range (e.g., a green colored region or "green zone") and a corresponding staple compression representation at each end of scale (130). By way of example only, as shown in FIG. 9, a first staple image (132) depicts a large staple height while a second staple image (134) depicts a small staple height. Accordingly, a user can view the position of the coupled anvil (40) relative to the stapling head assembly (200) via indicator bar (110) and scale (130). The user may then adjust the positioning of anvil (40) via adjustment knob (98) accordingly.

In the example shown in FIGS. 6-8, a U-shaped clip (100) is attached to an intermediate portion of trocar actuator (231) via a through hole (233) located distally of grooved shank (94). In the present example, an extension of trocar actuator (231) engages a slot in the housing of handle assembly (70) to prevent trocar actuator (231) from rotating about its axis when adjustment knob (98) is rotated. It may be necessary to calibrate the proper placement of trocar actuator (231) within instrument (10) such that indicator bar (110) may show a proper gap distance d during exemplary use. U-shaped clip (100) of the present example further includes an elongated slot (102) on each of its opposite sides for receiving an attachment member, such as a screw, bolt, pin, etc., to selectively adjust the longitudinal position of elongated slot (102) of U-shaped clip (100) relative to trocar actuator (231) for purposes of calibrating indicator bar (110) relative to scale (130). In some versions, the attachment member (e.g., screw, bolt, pin, etc.) engages with a portion of body (72) to substantially prevent trocar actuator (231) from rotating about its axis when adjustment knob (98) is rotated.

As shown in FIGS. 6-8, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (143) to slidably mount onto trocar actuator (231) and/or grooved shank (94). A coil spring (150) is interposed between flange (142) and a boss (152) of body (72) to bias flange (142) against U-shaped clip (100). Accordingly, when U-shaped clip (100) actuates distally with trocar actuator (231) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (231) and/or grooved shank (94) translate proximally, thereby compressing coil spring (150). In some versions, indicator bracket (140) may be fixedly attached to trocar actuator (231) and/or grooved shank (94).

In the present example, a portion of lockout feature (82) abuts a surface (141) of indicator bracket (140) when indicator bracket (140) is in a longitudinal position that does not correspond to when gap distance d is within a desired operating range (e.g., a green colored region or "green zone"). When gap distance d is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 7, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 9) to show the relative gap distance d between proximal surface (50) of anvil (40) and distally presented deck surface (222) of deck member (220).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847; and/or 9,936,949 the disclosures of which are incorporated by reference herein; and/or in accordance with other configurations as will be apparent to one of ordinary skill in the art in view of the teachings herein.

E. Exemplary Use of Circular Stapling Surgical Instrument

FIGS. 12A-12B and FIGS. 10A-10E show an exemplary use of circular stapling surgical instrument (10) in accordance with the description above. As mentioned above, anvil (40) may selectively couple with trocar (230) such that movement of trocar (230) relative to tubular casing (210) and deck member (220) leads to movement of anvil (40) relative to tubular casing (210) and deck member (220). With anvil (40) as a separate component, it should be understood that anvil (40) may initially be inserted and secured to a portion of tissue (2) prior to being coupled with trocar (230). By way of example only, anvil (40) may be inserted into and secured to a first tubular portion of tissue (2) while stapling head assembly (200) is inserted into and secured to a second tubular portion of tissue (2). For instance, the first tubular portion of tissue (2) may be sutured to or about a portion of anvil (40), and the second tubular portion of tissue (2) may be sutured to or about trocar (230).

As shown in FIG. 10A, anvil (40) may then be coupled to trocar (230) in accordance with the description above, such as a snap fitting between latch members (30) of anvil (40) and head (234) of trocar (230). In FIG. 10A, trocar (230) is shown in a distal most actuated position. Trocar (230) may be actuated to the distal most actuated position by rotation of knob (98) in accordance with the description above. Such an extended position for trocar (230) may provide a larger area to which tissue (2) may be coupled prior to attachment of anvil (40). The extended position of trocar (230) may also provide for easier attachment of anvil (40) to trocar (230). At the position shown in FIG. 10A, trigger (74) is locked in the position shown in FIG. 7A by lockout feature (82), as lockout feature (82) may not pivot to unlock trigger (74) due to interference caused by surface (141) of indicator bracket (140) in accordance with the description above.

As mentioned above, when anvil (40) is coupled to trocar (230), rotation of adjustment knob (98) may translate both trocar (230) and anvil (40), thereby enlarging or reducing gap distance d. For instance, as shown sequentially in FIGS. 10A-10B, anvil (40) is shown actuating proximally relative to actuator handle assembly (70) from an initial, open position (FIG. 10A) to a closed position (FIG. 10B) where gap distance d is brought within a suitable predetermined range. It should be understood that in the position shown in FIG. 10A, grooved shank (94) is in a distal position where the middle portion (96B) of groove (96) engages internal tab (95) of sleeve (92).

When gap distance d is brought within a suitable predetermined range, indicator bar (110) may move within indicator window (120) to show the relative gap distance d is within a desired operating range (e.g. a green colored region or "green zone") in accordance with the description above.

Likewise, it should be understood that in the position shown in FIG. 10B, grooved shank (94) is in a proximal position where the proximal portion (96C) of groove (96) engages internal threading (97) of knob (98). Therefore, each rotation of adjustment knob (98) may reduce the gap distance d by a relatively small amount to provide for fine tuning.

Figure 10C:
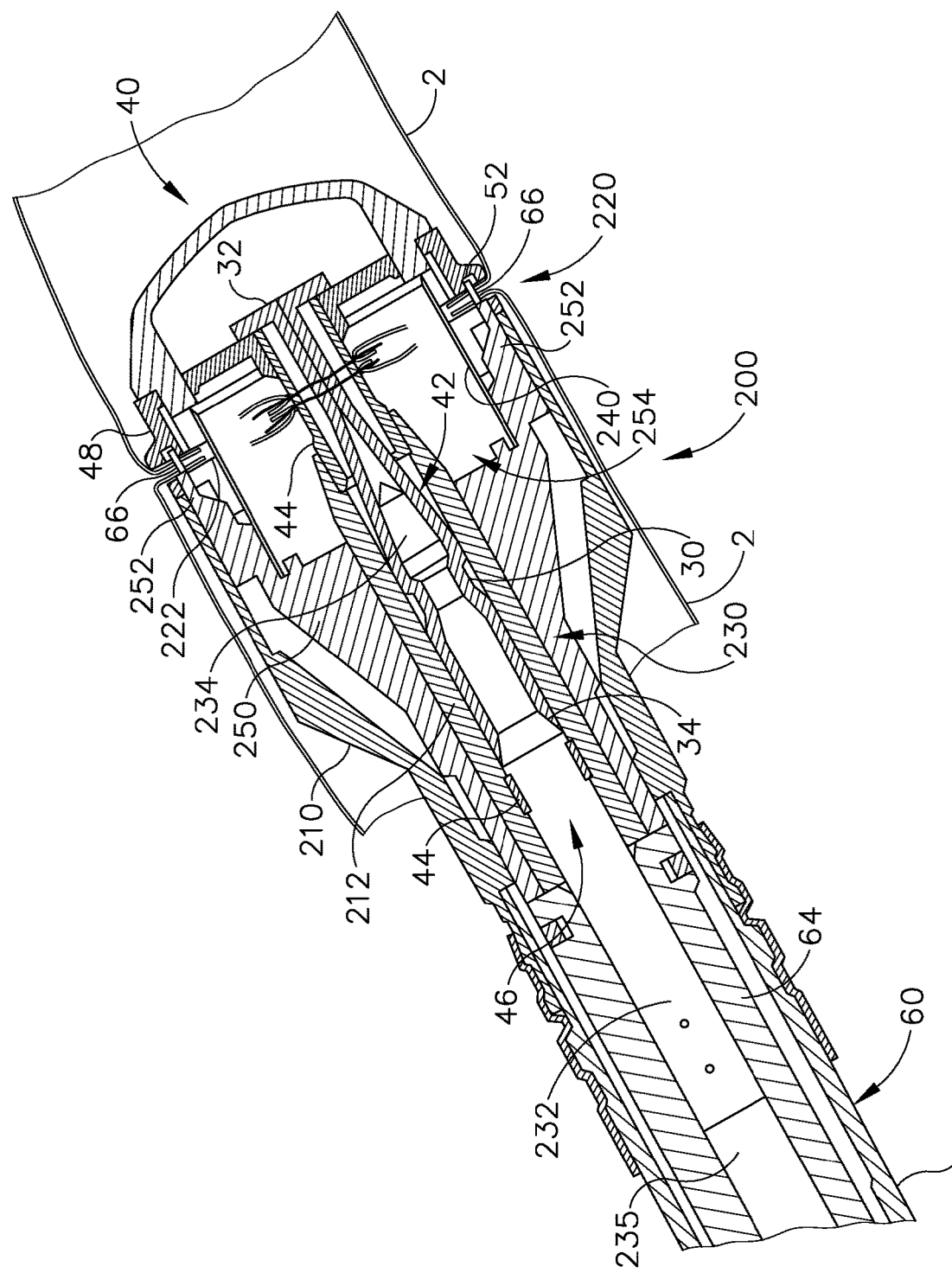
FIG. 10C depicts an enlarged longitudinal cross-sectional view of the stapling head assembly of FIG. 5, showing the anvil of FIG. 2 in the closed position, were an exemplary staple driver and blade are in a fired position such that the first tubular portion of tissue and the second tubular portion of tissue are stapled together with excess tissue severed.

As shown between FIGS. 12A-12B, when gap distance d is brought within a suitable predetermined range, lockout feature (82) may be pivoted relative to body (72) to an unlocked position such that trigger (74) may pivot relative to body (72) to engage trigger actuation assembly (84) in accordance with the description above. As shown in FIG. 12B, with lockout feature (82) pivoted into the unlocked position, trigger (74) is pivoted toward body (72) such that trigger arms (76) drive against tabs (88) to distally actuate slidable trigger carriage (86) and driver actuator (64). As shown in FIG. 10C, distal actuation of driver actuator (64) drives slidable staple driver member (250), staples drivers (252), and cylindraceous knife member (240) distally. Distal advancement of staple drivers (252) drive staples (66) against corresponding staple forming pockets (52) thereby stapling tissue (2) between anvil (40) and stapling head assembly (200) to form a continuous tubular portion of tissue (2). Additionally, distal advancement of cylindraceous knife member (240) severs excess tissue located radially interior to newly formed staples (66). Stapling head assembly (200) is operable to staple and sever tissue (2) by a user pivoting a trigger (74) of actuator handle assembly (70), as will be described in greater detail below.

Figure 10D:
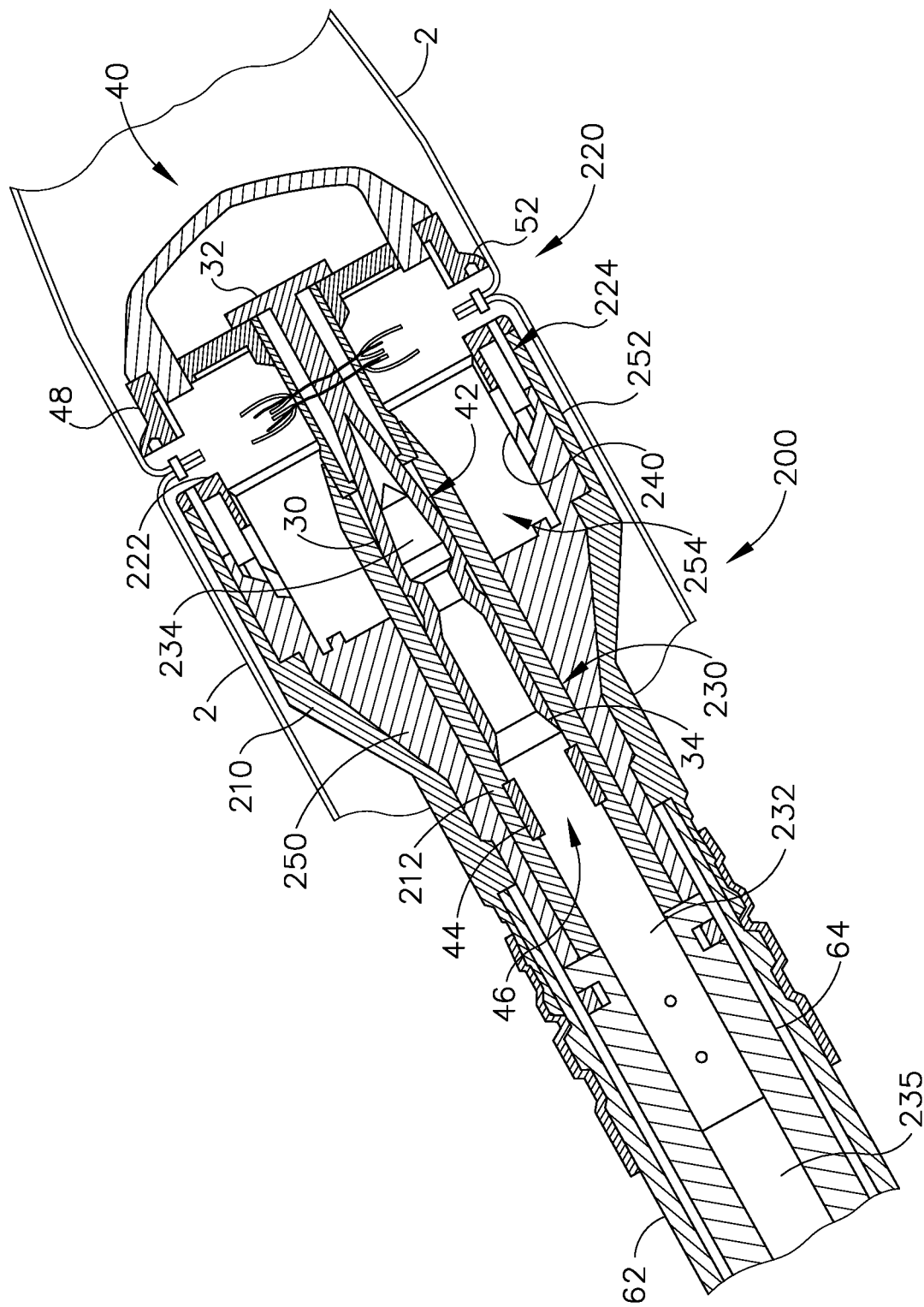
FIG. 10D depicts an enlarged longitudinal cross-sectional view of the stapling head assembly of FIG. 5, showing the anvil of FIG. 2 in a second open position, where the first tubular portion of tissue and the second tubular portion of tissue are attached.
Figure 10E:
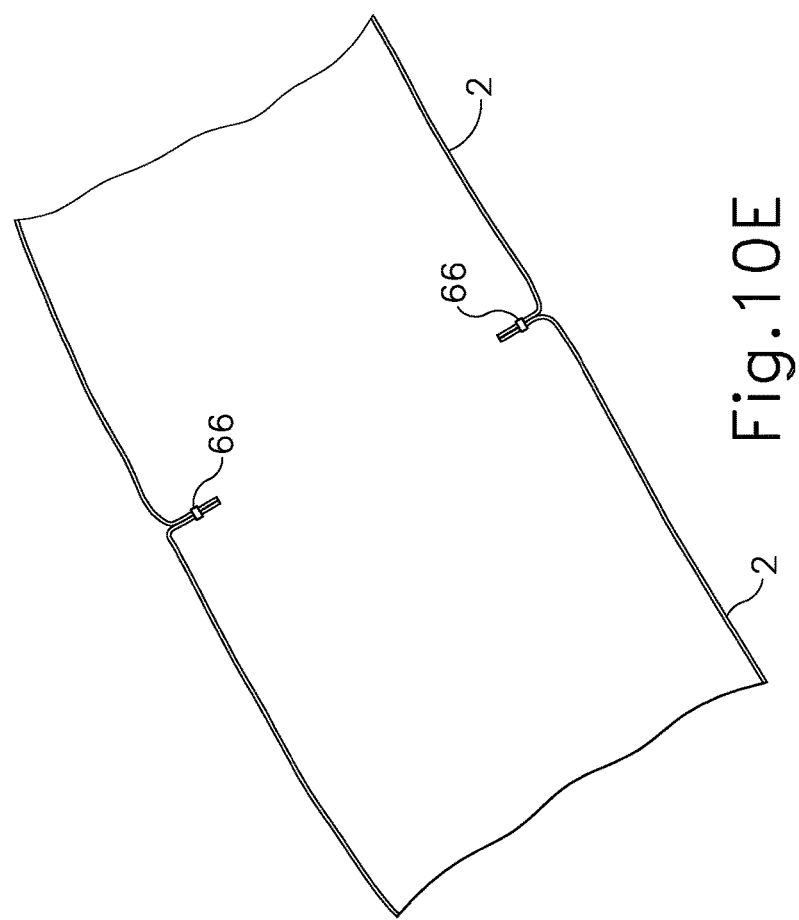
FIG. 10E depicts an enlarged longitudinal cross-section view of the first tubular portion and the second tubular portion after the stapling head assembly of FIG. 5 and the anvil of FIG. 2 have been removed, leaving a completed end-to-end anastomosis.
Figure 11:
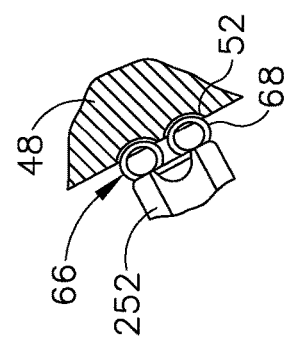
FIG. 11 depicts an enlarged partial cross-sectional view of an exemplary staple formed against the anvil of FIG. 2.

As best shown in FIG. 10D, once trigger (74) has been actuated to staple and sever tissue (2), a user may then turn rotatable knob (98) to distally advance anvil (40), thereby releasing portions of tissue (2) grasped between proximal surface (50) of anvil (40) and distally presented deck surface (222) of deck member (220). As best shown in FIG. 10E, with previously grasped tissue (2) released, a user may then remove instrument (10), thereby leaving a continuous tubular portion of tissue (2) behind.

II. Exemplary Trocar Latch Assemblies for Circular Stapling Surgical Instrument

Those of ordinary skill in the art will recognize that an appropriate gap distance d may be particularly critical to the success of an anastomosis. It may therefore be critical for the operator to be assured that the gap distance d is consistently and precisely achieved in accordance with the operator's expectations based on the angular position of adjustment knob (98); and based on the accuracy of indicator bar (110) displaying gap distance d. However, tissue (2) captured between anvil (40) and deck member (220) may require high compressive forces to ensure gap distance d is within a desired operating range. Because anvil (40) is coupled with trocar (230) when anvil (40) is actuated proximally toward deck member (220) to provide a suitable gap distance d, these forces are transferred from anvil (40) to trocar (230), flexible band portion (235), and trocar actuator (231) in the form of tension.

Tensile forces imparted on trocar (230), flexible band portion (235), and trocar actuator (231) may increase when staple driver member (250) and cylindraceous knife member (240) are actuated distally to staple and sever tissue. This increase in tensile force may cause unwanted distal translation of trocar (230), flexible band portion (235), and trocar actuator (231) during exemplary use, as the increased tensile forces may cause groove (96) to rotate adjustment knob (98). In effect, gap distance d may undesirably deviate (e.g., expand) during distal translation of staple driver member (250) and cylindraceous knife member (240) compared to when the operator confirmed a desirable gap distance d via window (120). Therefore, it may be desirable to help prevent unwanted translation of trocar (230) during the firing of firing system such that gap distance d does not deviate due to increased tensile forces within the closure system.

Figure 13A:
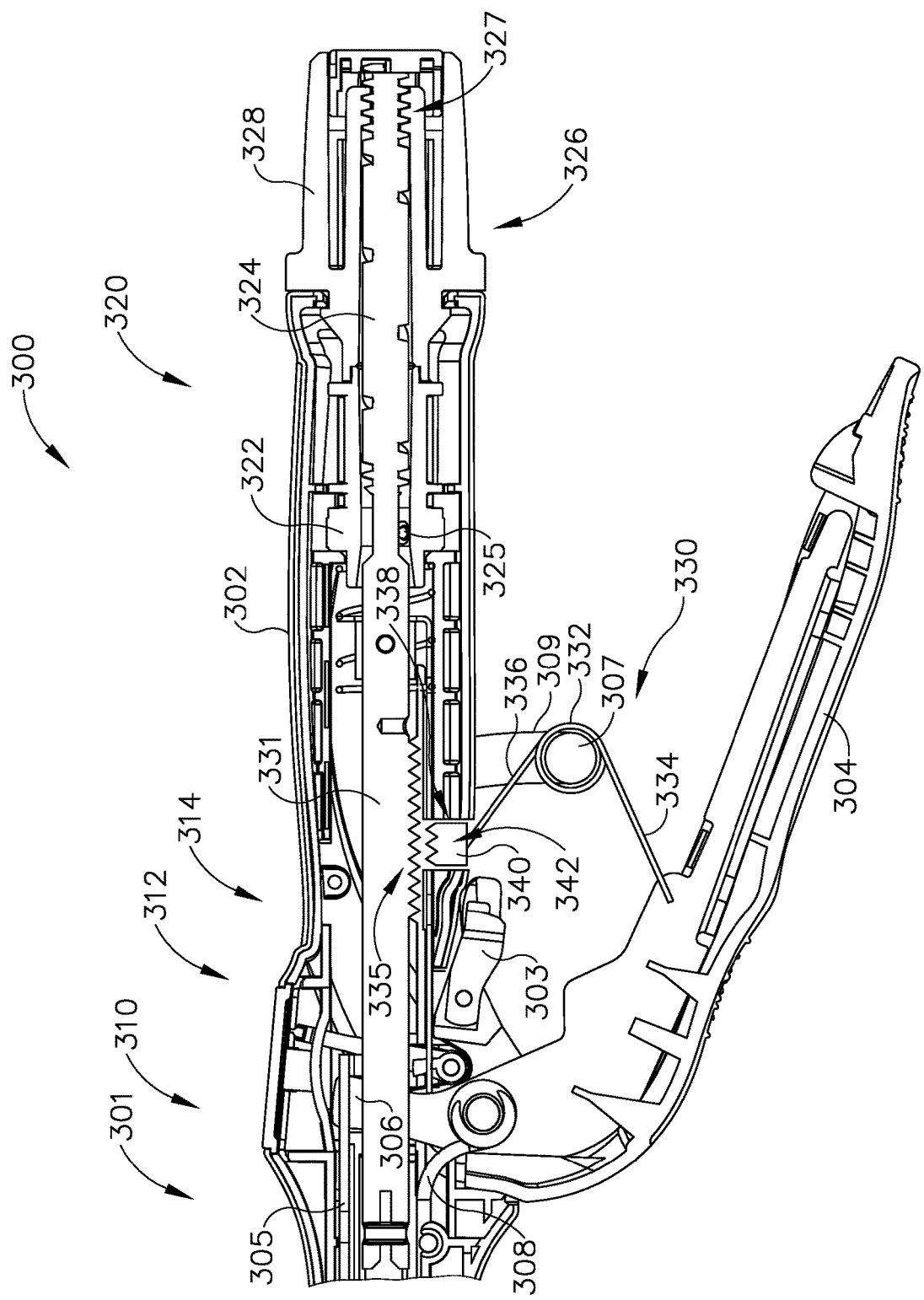
FIG. 13A depicts a cross-sectional side view of an alternative actuator handle assembly that may be readily incorporated into the surgical instrument of FIG. 1, showing a trigger in an unfired positioned and a trocar latch assembly in an unlatched position.
Figure 13B:
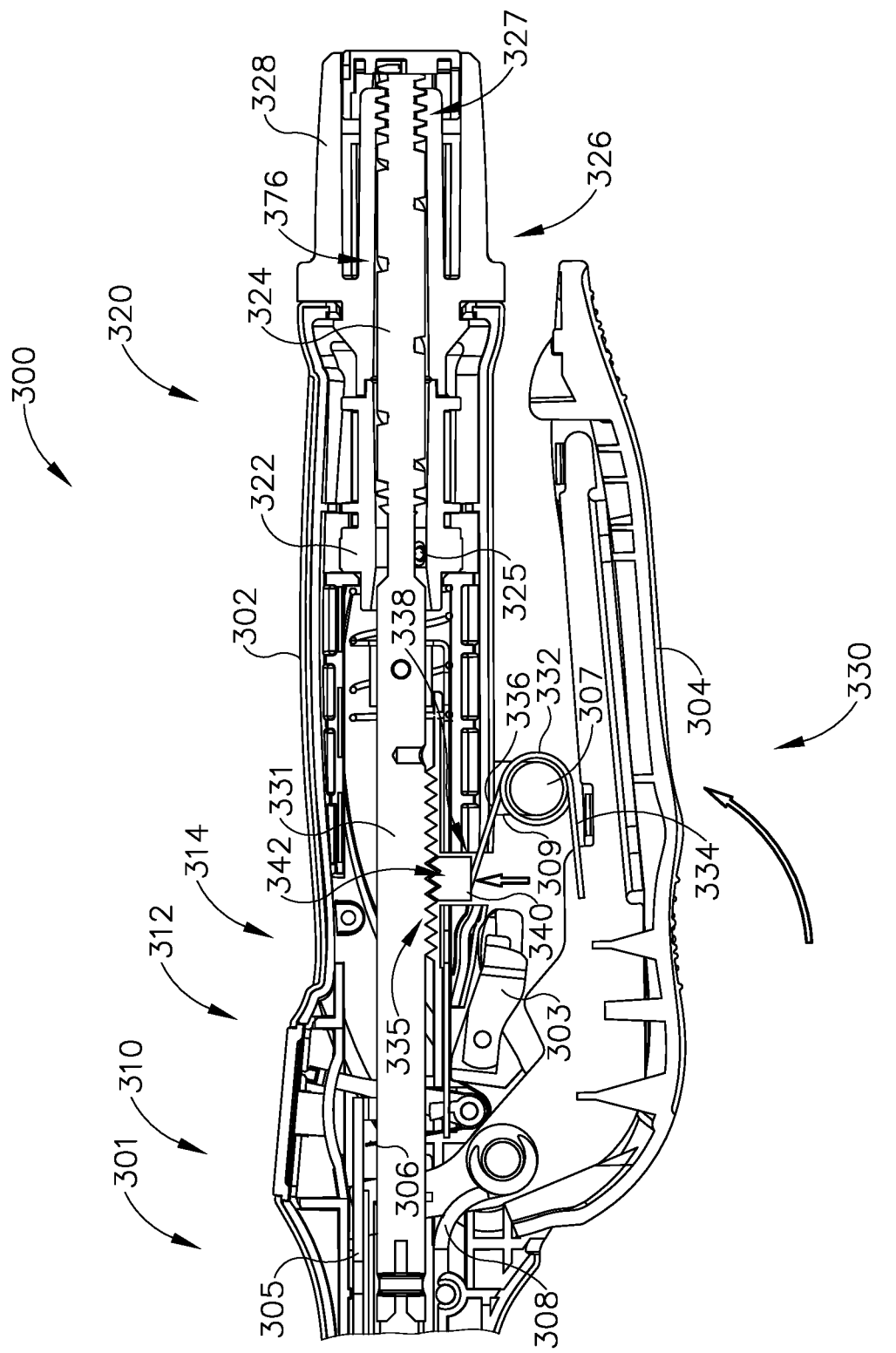
FIG. 13B depicts a cross-sectional side view of the actuator handle assembly of FIG. 13A, showing the trigger in a fired position and the trocar latch assembly in a latched position.

FIGS. 13A-13B show an exemplary alternative actuator handle assembly (300) that may be readily incorporated into surgical instrument (10) in replacement of actuator handle assembly (70) described above. Actuator handle assembly (300) is substantially similar to actuator handle assembly (70), with differences elaborated below. In particular, actuator handle assembly (300) includes a trocar latch assembly (330) configured to help prevent unwanted translation of a trocar actuator (331) relative to a body (302) during exemplary firing of firing system, which in turn may help prevent unwanted deviation of gap distance d as described herein.

Actuator handle assembly (300) includes body (302), a trigger (304), a lockout feature (303), a spring (308), a trigger actuation assembly (301), a trocar actuation assembly (320), an indicator window (310), an indicator (312), and an indicator bracket (314); which are substantially similar to body (72), trigger (74), lockout feature (82), spring (78), trigger actuation assembly (84), trocar actuation assembly (90), indicator window (120), indicator (104), and indicator bracket (140) as described above respectively, with differences described below.

Therefore, trigger (304) includes trigger arms (306) that are substantially similar to trigger arms (76) described above, while trigger actuation assembly (301) includes slidable trigger carriage (305) that is substantially similar to slidable trigger carriage (86) described above. Therefore, pivoting trigger (304) toward body (302) while lockout feature (303) is in the unlocked position will drive staple driver member (250) and cylindraceous knife (240) distally, while pivoting trigger (304) away from body (302) will drive staple driver member (250) and cylindraceous knife (240) proximally.

Trocar actuation assembly (320) includes an adjustment knob (328), a sleeve (322), a grooved shank (324), and a trocar actuator (331), which are substantially similar to adjustment knob (98), sleeve (92), grooved shank (94), and trocar actuator (231) described above, respectively, with differences elaborated below. Adjustment knob (328) includes internal threading (327), which is substantially similar to internal threading (97) described above. Sleeve (322) includes an internal tab (325) which is substantially similar internal tab (95) described above. Grooved shank (324) includes a continuous groove (326) that is substantially similar to continuous groove (96) described above. Therefore, adjustment knob (328) and sleeve (322) may rotate relative to body (302) in order to linearly actuate grooved shank (324) and trocar actuator (331) in accordance with the description above.

As mentioned above, and as will be described in greater detail below, actuator handle assembly (300) includes trocar latch assembly (330), which is configured to help prevent unwanted translation of trocar actuator (331) relative to body (302) during exemplary firing of firing system. Trocar latch assembly (330) includes a spring (332), an array of gripping teeth (335) disposed on an exterior surface of trocar actuator (331), and a latch block (340) slidably disposed within a channel (338) defined by body (302). Array of griping teeth (335) are disposed on trocar actuator (331) such that when gap distance d is within the desired operating range, a portion of gripping teeth (335) is directly adjacent to channel (338), and therefore latch block (340).

Latch block (340) is slidably disposed within channel (338) such that latch block (340) may actuate vertically while being longitudinally constrained relative to body (302). Latch block (340) includes complementary teeth (342) dimensioned to engage corresponding gripping teeth (335). As will be described in greater detail below, latch block (340) is configured to actuate vertically within channel (338) between a disengaged position (as shown in FIG. 13A) and an engaged position (as shown in FIG. 13B). Because latch block (340) is longitudinally constrained within channel (338), when latch block (340) engages trocar actuator (331) via a frictional braking force between gripping teeth (335, 342), trocar actuator (331) is inhibited from actuating longitudinally via the frictional braking force.

Spring (332) includes a first leg (334) and a second leg (336). First leg (334) is connected to trigger (304) while second leg (336) is connected to latch block (340). Additionally, spring (332) may be coupled with body (302) via a downwardly presented arm (309) and rod (307) of body (302), where rod (307) extends through the interior of spring (332) to fix the coil portion of spring (332) relative to body (302). Legs (334, 336) of spring (332) are dimensioned such that when trigger (304) is in the open position (as shown in FIG. 13A), latch block (340) is in a position within channel (338) while also being disengaged with array of gripping teeth (335). Therefore, when trigger (304) is in the open position, the operator may freely rotate adjustment knob (328) to achieve a desirable gap distance d in accordance with the description above.

Legs (334, 336) of spring (332) are dimensioned such that when trigger (304) is initially pivoted toward the closed position (as shown in FIG. 13B), spring (332) drives latch block (340) within channel (338) such that latch block (340) engages trocar actuator (331) via teeth (335, 342). Legs (334, 336) of spring (332) may be dimensioned such that latch block (340) engages trocar actuator (331) at any suitable time during the pivoting of trigger (304) toward the closed position that would be apparent to one having ordinary skill in the art in view of the teachings herein. Latch block (340) may remain engaged with trocar actuator (331) until trigger (304) is pivoted back to the open position such that spring (332) drives latch block (340) back to the disengaged position. Therefore, spring (332) is dimensioned such that latch block (340) engages trocar actuator (331) based on the pivotable position of trigger (304).

It should be understood that when trigger (304) is pivoted toward the closed position, trigger actuation assembly (301) starts to drive slidable staple driver member (250) and cylindraceous knife member (240) distally, thereby increasing the tensile force within trocar (230). As mentioned above, this increased tensile force may lead to undesirable distal movement of trocar actuator (331), which can adversely impact gap distance d. However, since latch block (340) is longitudinally constrained within channel (338), when trigger (304) is initially pivoted toward the closed position, latch bock (340) may remain engaged with trocar actuator (331) until trigger (304) is pivoted back toward the open position (as shown in FIG. 13A). Therefore, latch block (340) may prevent actuation of trocar actuator (331) during exemplary firing of firing system such that gap distance d does not undesirably deviate between the operator visually confirming gap distance d and the operator stapling and severing tissue. With slidable staple driver member (250) and cylindraceous knife member (240) returned to the pre-fired position, and with latch block (340) in the disengaged position, the operator may adjust gap distance d in accordance with the description above.

Figure 14A:
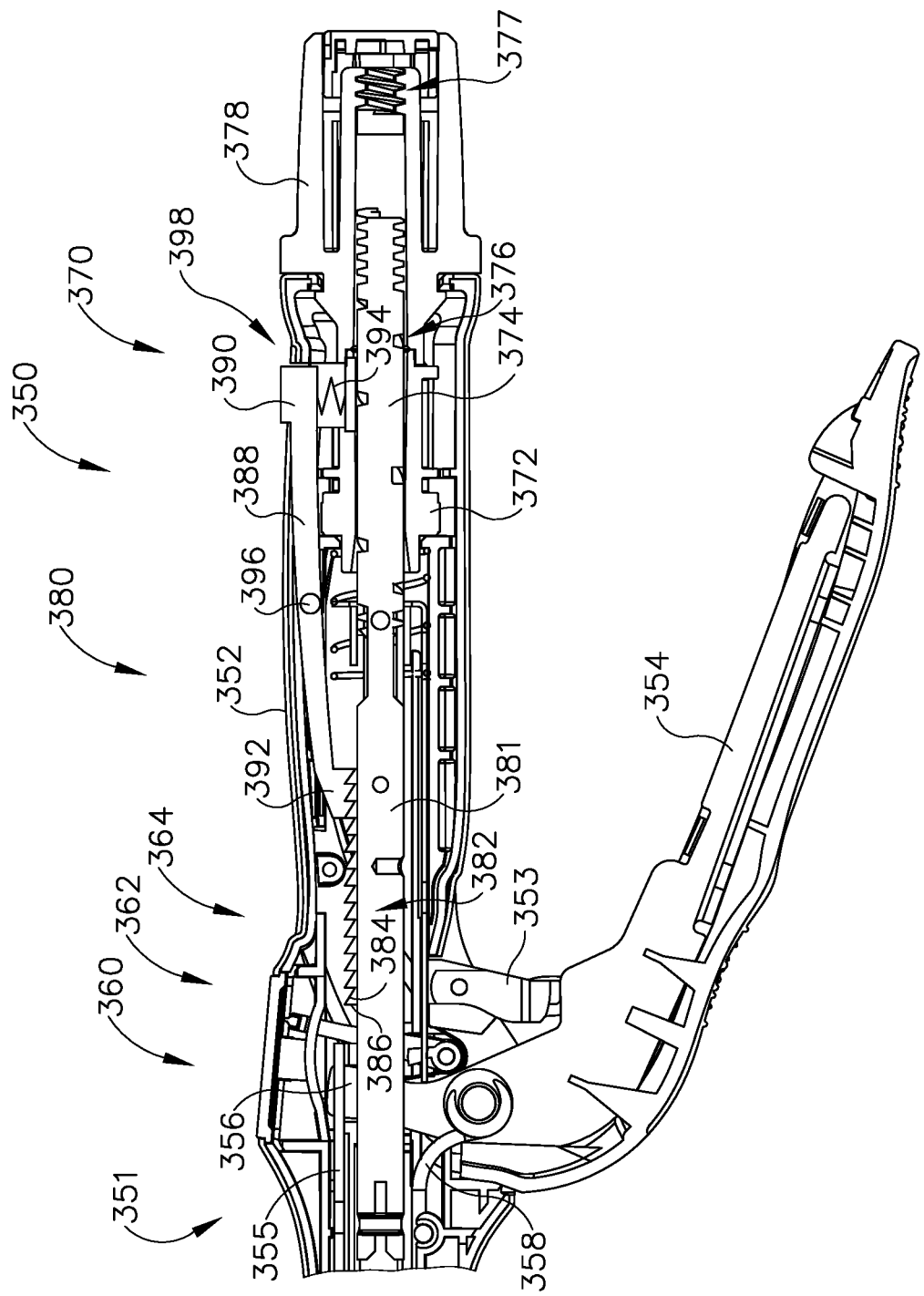
FIG. 14A depicts a cross-sectional side view of an alternative actuator handle assembly that may be readily incorporated into the surgical instrument of FIG. 1, where the trocar actuator is in a position associated with the anvil in the first open position shown in FIG. 10A, where a latch assembly is in a locked position.
Figure 14B:
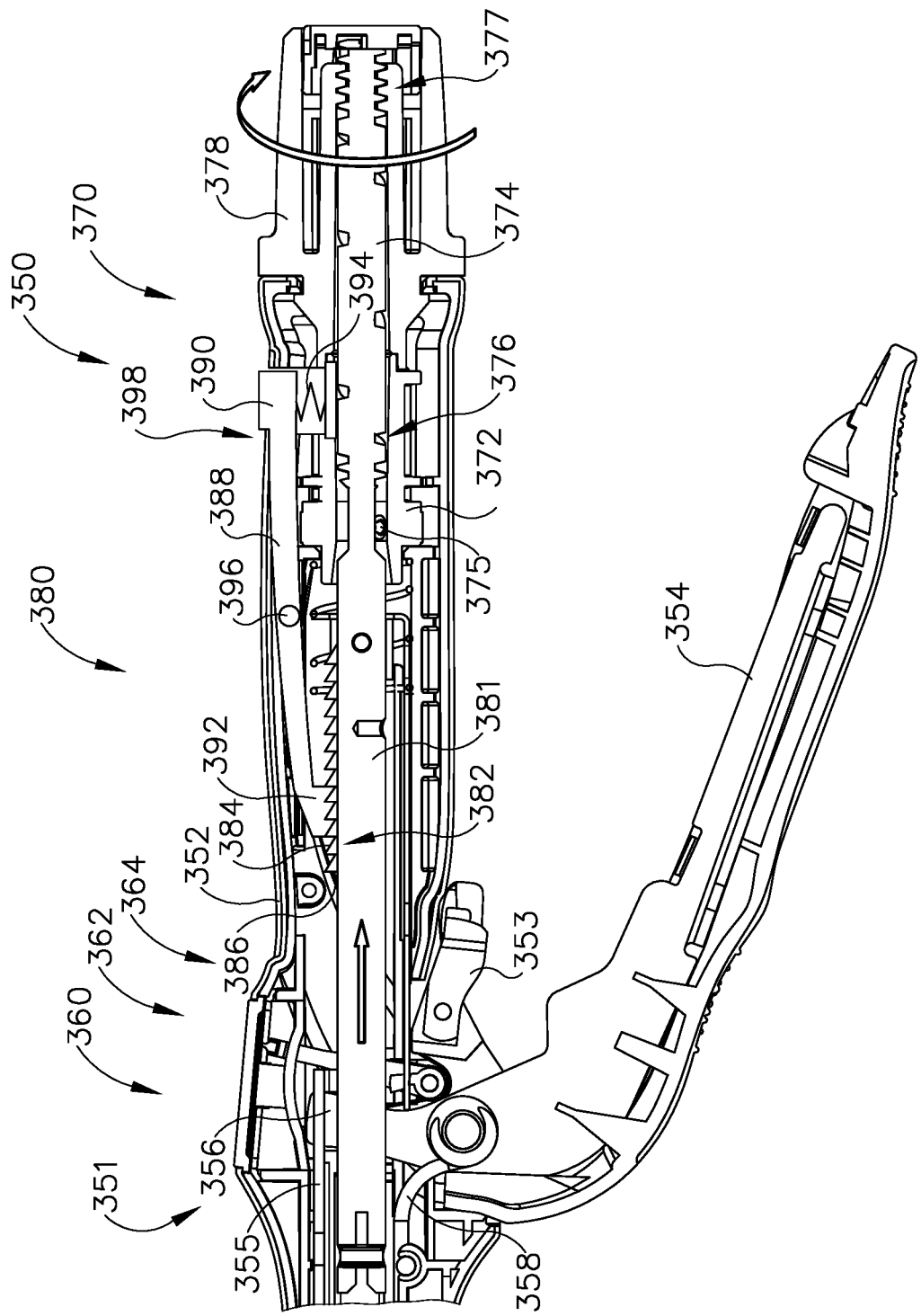
FIG. 14B depicts a cross-sectional side view of the actuator handle assembly of FIG. 14A, where the trocar actuator is in a position associated with the anvil in the closed position shown in FIG. 10B, where the latch assembly of FIG. 14A is in the locked position.

FIGS. 14A-14C show another exemplary alternative actuator handle assembly (350) that may be readily incorporated into surgical instrument (10) in replacement of actuator handle assembly (70) described above. Actuator handle assembly (350) is substantially similar to actuator handle assembly (70), with differences elaborated below. In particular, actuator handle assembly (350) includes a trocar ratcheting latch assembly (380) configured to actuate between an engaged position and a disengaged position. Ratcheting latch assembly (380) is configured to help prevent unwanted distal translation of a trocar actuator (381) relative to body (352) while ratcheting latch assembly (380) is in the engaged position, which in turn may help prevent unwanted deviation of gap distance d in accordance with the description herein. Additionally, ratcheting latch assembly (380) may selectively actuate from the engaged position to the disengaged position to allow distal translation of trocar actuator (381) relative to body (352).

Actuator handle assembly (350) includes body (352), a trigger (354), a lockout feature (353), a spring (358), a trigger actuation assembly (351), a trocar actuation assembly (370), an indicator window (360), an indicator (362), and an indicator bracket (364); which are substantially similar to body (72), trigger (74), lockout feature (82), spring (78), trigger actuation assembly (84), trocar actuation assembly (90), indicator window (120), indicator (104), and indicator bracket (140) as described above respectively, with differences described below.

Therefore, trigger (354) includes trigger arms (356) that are substantially similar to trigger arms (76) described above, while trigger actuation assembly (351) includes slidable trigger carriage (355) that is substantially similar to slidable trigger carriage (86) described above. Therefore, pivoting trigger (354) toward body (352) while lockout feature (353) is in the unlocked position will drive staple driver member (250) and cylindraceous knife (240) distally, while pivoting trigger (354) away from body (352) will drive staple driver member (250) and cylindraceous knife (240) proximally.

Trocar actuation assembly (370) includes an adjustment knob (378), a sleeve (372), a grooved shank (374), and a trocar actuator (381), which are substantially similar to adjustment knob (98), sleeve (92), grooved shank (94), and trocar actuator (231) described above, respectively, with differences elaborated below. Adjustment knob (378) includes internal threading (377), which is substantially similar to internal threading (97) described above. Sleeve (372) includes an internal tab (375) which is substantially similar internal tab (95) described above. Grooved shank (374) includes a continuous groove (376) that is substantially similar to continuous groove (96) described above. Therefore, adjustment knob (378) and sleeve (372) may rotate relative to body (352) in order to linearly actuate grooved shank (374) and trocar actuator (381) in accordance with the description above.

As mentioned above, and as will be described in greater detail below, actuator handle assembly (300) includes trocar ratcheting latch assembly (380), which is configured to help prevent unwanted distal translation of trocar actuator (381) relative to body (352) while ratcheting latch assembly (380) is in the engaged position. Ratcheting latch assembly (380) includes an array of angled teeth (382) disposed on an exterior surface of trocar actuator (381) and a rotating link (388) pivotably coupled to body (352) via a pivot pin (396). Each tooth in array of angled teeth (382) include a proximal slanted surface (384) and a distal shoulder (386). Array of angled teeth (382) are disposed on trocar actuator (381) such that when gap distance d is within the desired operating range, a portion of angled teeth (383) are directly adjacent to pawl (392) of rotating link (388). As will be described in greater detail below, proximal slanted surfaces (384) are dimensioned to allow proximal translation of trocar actuator (381) while ratcheting latch assembly (380) is in the engaged position; while distal shoulders (386) are dimensioned to inhibit distal translation of trocar actuator (381) while ratcheting latch assembly (380) is in the engaged position.

Rotating link (388) extends between a proximal button (390) and distal pawl (392). Body (352) defines a recess (398) that houses button (390) such that button (390) may pivot within recess (398). A bias spring (394) biases rotating link (388) toward the engaged position. Pawl (392) includes complementary teeth configured to engage angled teeth (382) on trocar actuator (381) in the engaged position. The complementary teeth of pawl (392) allow proximal translation of trocar actuator (381), while inhibiting distal translation of trocar actuator (381), when ratcheting latch assembly (380) is in the engaged position. In particular, proximal slanted surfaces (384) of teeth (382) cam against pawl (392) such that pawl (392) pivots upward in a ratcheting fashion during proximal translation of trocar actuator (381). The complementary teeth of pawl (392) abut against distal shoulder (386) of teeth (382) to inhibit distal translation of trocar actuator (381). Because rotating link (388) is attached to body (352), The operator may push down on button (390) when desirable to overcome the biasing force of spring (394) such that button (390) pivots within recess (398) and pawl (392) pivots away from array of angled teeth (382). With pawl (392) pivoted away from array of angled teeth (382), ratcheting latch assembly (380) is in the disengaged position such that trocar actuator (381) may translate proximally and distally relative to body (352).

FIGS. 14A-14C show an exemplary use of ratcheting latch assembly (380). First, as shown between FIGS. 14A-14B, the operator may rotate adjustment knob (378) to translate trocar actuator (381) proximally while trocar (230) is suitably attached to anvil (40). The operator may rotate adjustment knob (378) to achieve a desirable gap distance d in accordance with the description above. It should be understood that spring (394) biases pawl (392) into engagement with teeth (382) between FIGS. 14A-14B such that ratcheting latch assembly (380) is in the engaged position. Therefore, ratcheting latch assembly (380) prevents distal translation of trocar actuator (381).

When a desirable gap distance d is achieved, the operator may pivot lockout feature (353) to the unlocked position, and further pivot trigger (354) to staple and sever tissue between anvil (40) and staple head assembly (200) in accordance with the description herein. It should be understood that when trigger (354) is pivoted toward the closed position, trigger actuation assembly (351) starts to drive slidable staple driver member (250) and cylindraceous knife member (240) distally, thereby increasing the tensile force within trocar (230). As mentioned above, this increased tensile force may lead to undesirable distal movement of trocar actuator (381), which can adversely impact gap distance d. However, since ratcheting latch assembly (380) is in the engaged position, engagement between pawl (392) and trocar actuator (381) via teeth (382) helps inhibit trocar actuator (381) from actuating distally. Therefore, pawl (392) may prevent actuation of trocar actuator (381) during exemplary firing of firing system such that gap distance d does not undesirably deviate between the operator visually confirming gap distance d and the operator stapling and severing tissue.

Once firing is complete, as shown in FIG. 14C, the operator may press button (390) downward to actuate pawl (392) into a disengaged position. The operator may then rotate knob (378) with pawl (392) in the disengaged position such that trocar actuator (381), and therefore anvil (40), actuates distally thereby releasing portions of tissue (2) grasped between proximal surface (50) of anvil (40) and distally presented deck surface (222) of deck member (220).

Figure 15A:
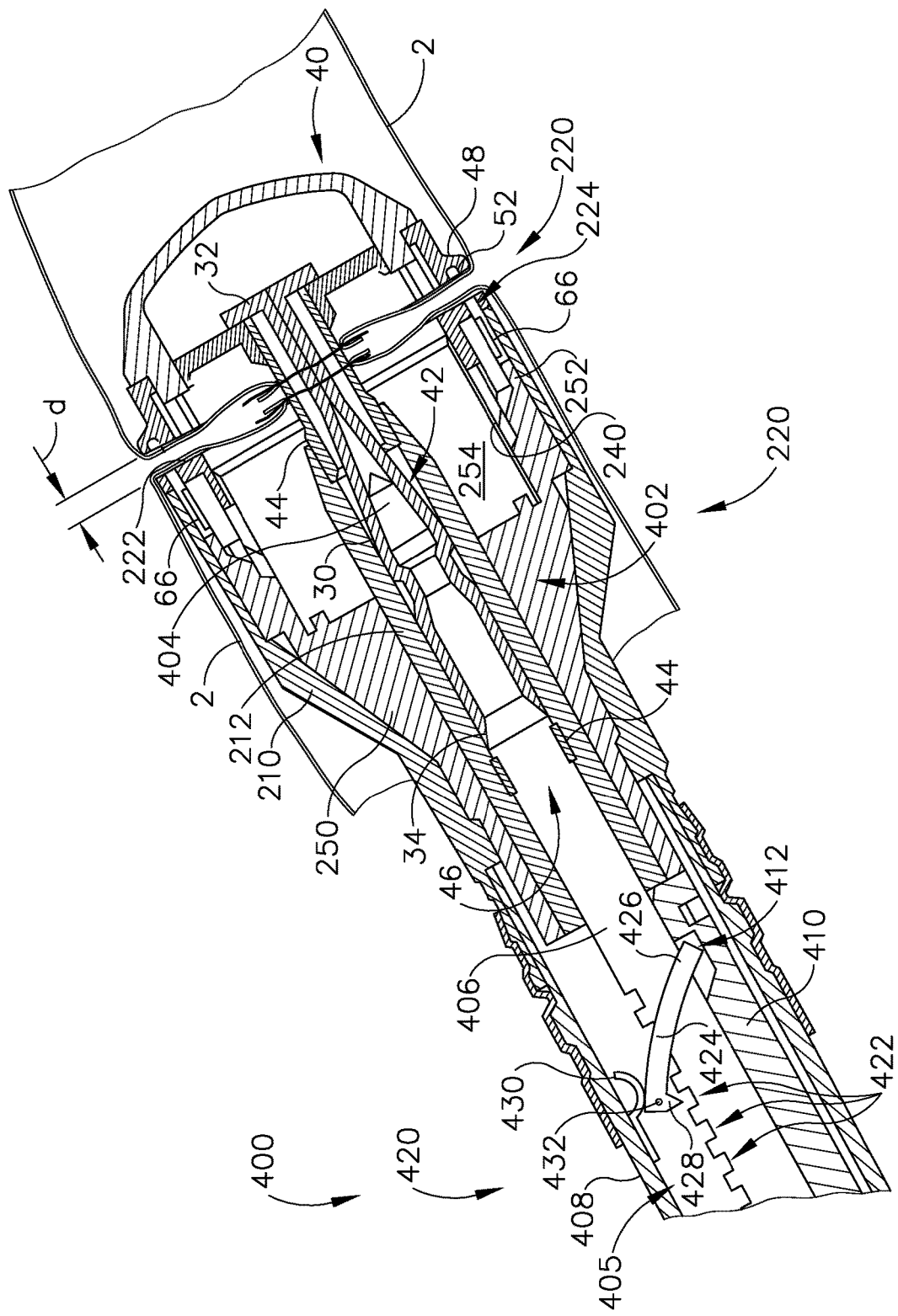
FIG. 15A depicts a cross-sectional side view of an alternative shaft assembly attached to the stapling head assembly of FIG. 5, showing the anvil of FIG. 2 in a closed position, where the anvil is within the first tubular portion of tissue and the stapling head assembly is within the second tubular portion of tissue, where the stapling head assembly is in the unfired position and a latch assembly is in an unlocked position.
Figure 15B:
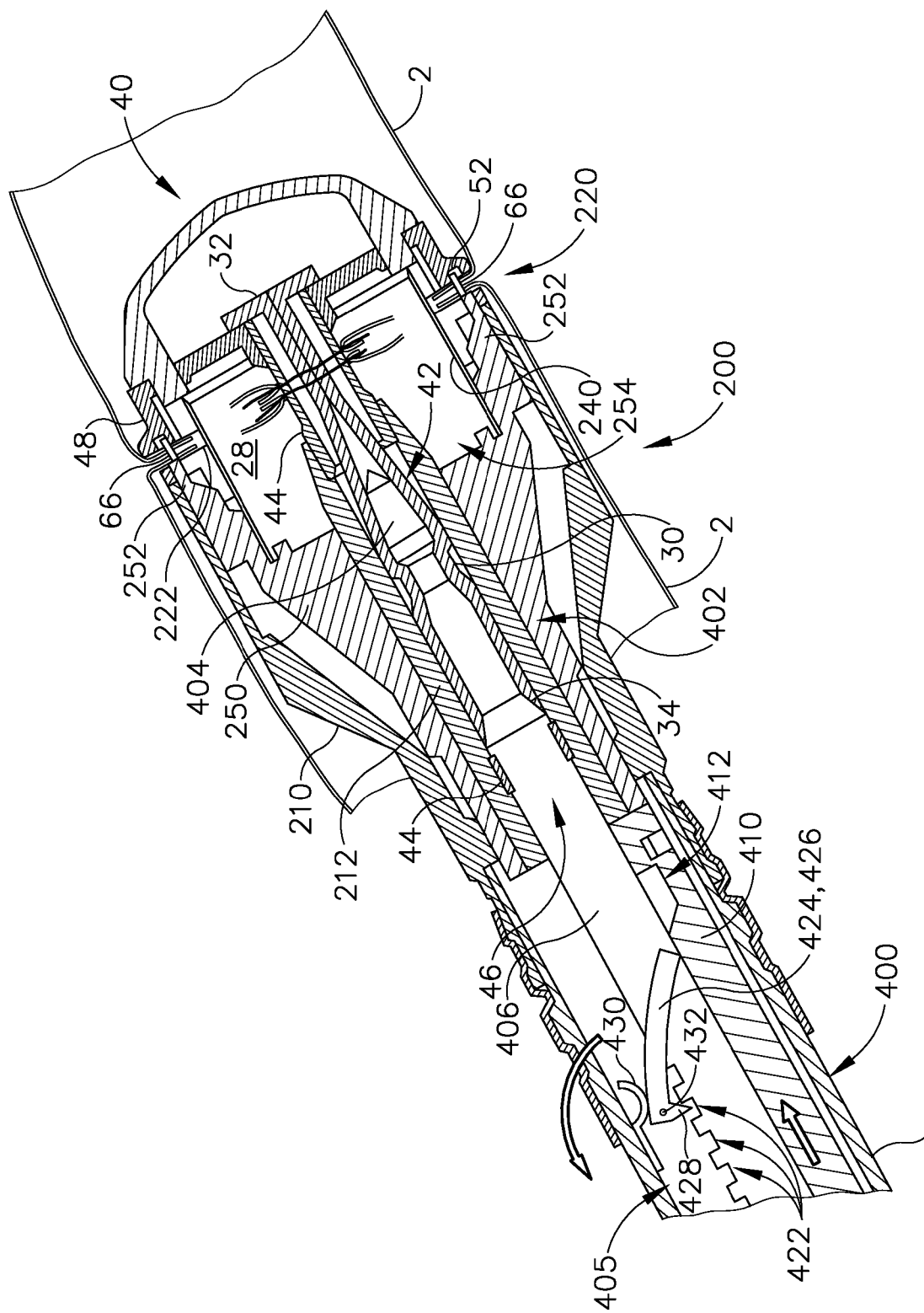
FIG. 15B depicts a cross-sectional side view of the shaft assembly of FIG. 15A attached to the stapling head assembly of FIG. 5, showing the anvil of FIG. 2 in a closed position, were an exemplary staple driver and blade are in a fired position such that the first tubular portion of tissue and the second tubular portion of tissue are stapled together with excess tissue severed and the latch assembly is in a locked position.

FIGS. 15A-15B show an alternative shaft assembly (400) readily incorporated into instrument (10) in replacement of shaft assembly (60) described above. Therefore, shaft assembly (400) is substantially similar to shaft assembly (60) described above, with differences elaborated below. Shaft assembly (400) includes trocar latch assembly (420) configured to help prevent unwanted translation of a trocar (402) relative to an outer tubular member (408) during exemplary firing of firing system, which in turn may help prevent unwanted deviation of gap distance d as described herein.

Shaft assembly (400) includes alternative trocar (402), alternative outer tubular member (408), and an alternative driver actuator (410); which are substantially similar to trocar (230), outer tubular member (62), and driver actuator (64) described above, with differences elaborated below. Therefore, trocar (402) includes a head (404) and a shaft (406) that are substantially similar to head (234) and shaft (232) described above. Trocar (402) is suitably coupled to adjustment knob (98) such that rotation of adjustment knob (98) actuates trocar (402) relative to outer tubular member (408) and driver actuator (410).

Outer tubular member (408) is coupled to tubular casing (210) of stapling head assembly (200) and to a body (72) of actuator handle assembly (70), thereby providing a mechanical ground for the actuating components therein. Similar to driver actuator (64) described above, the proximal end of driver actuator (410) is coupled to a trigger actuation assembly (84) of actuator handle assembly (70) while the distal end of driver actuator (410) is coupled to staple driver member (250). Therefore, the rotation of trigger (74) longitudinally actuates both driver actuator (410) and staple driver member (250).

As mentioned above, trocar latch assembly (420) is configured to prevent unwanted translation of trocar (402) when driver actuator (410) fires staple driver member (250) to sever and staple tissue in accordance with the description herein. Trocar latch assembly (420) includes a pivoting latch (424) pivotably attached to tubular member (408) via a pivot pin (432), and a leaf spring (430) attached to the interior of outer tubular member (408). Trocar (402), outer tube (408), and driver actuator (410) together define a channel (405) that houses pivoting latch (424) and leaf spring (430) such that pivoting latch (424) may rotate between an unlocked position and a locked position in accordance with the description herein. Additionally, trocar (402) defines an array of recesses (422) while driver actuator (410) defines a cutout (412). As will be described in greater detail below, distal actuation of driver actuation (410) is configured to drive pivoting latch (424) into engagement with one recess (422) of the array of recesses (422) in order to help inhibit translation of trocar (402) relative to outer tubular member (408) and staple head assembly (200), thereby helping ensure a consistent gap distance d during exemplary firing of driver actuator (410).

Pivoting latch (424) includes leg (426) and a locking body (428). As best seen in FIG. 15A, leaf spring (430) biases pivoting latch (424) such that an end of leg (426) rests within cutout (412) of driver actuator (410) and such that locking body (428) is disengaged with trocar (402). At this moment, trocar latch assembly (420) is in the unlocked position such that the operator may rotate adjustment knob (98) in order to actuate trocar (402) to change gap distance d. Therefore, leaf spring (430) biases trocar latch assembly (420), and pivoting latch (424) into the unlocked position. Array of recesses (422) span along trocar (402) such that at least one recess (422) is adjacent to locking body (428) of pivoting latch (424) when trocar (402) is located at any position associated with gap distance d being with a suitable predetermined range.

It should be understood that at the position shown in FIG. 15A, trocar (402) is suitably coupled with anvil (40) such that anvil (40) and staple head assembly (200) defined a gap distance d having a suitable predetermined range. Therefore, the operator may actuate firing assembly in order to sever and staple tissue in accordance with the description herein. With gap distance d residing within the suitable predetermined range, the operator may pivot lockout feature (82) to the unlocked position as described above.

When a desirable gap distance d is achieved, as shown in FIG. 15B, the operator may pivot trigger (74) toward body (72) to distally drive driver actuator (410) and staple driver member (250) in accordance with the description above. It should be understood that when trigger (74) is pivoted toward the closed position, distal actuation of driver actuator (410) increases the tensile force within trocar (230). As mentioned above, this increased tensile force may lead to undesirable distal movement of trocar (402), which can adversely impact gap distance d.

However, as driver actuator (410) translates distally within outer tubular member (408), the end of leg (426) cams against an interior surface of driver actuator (410) defining cutout (412) and/or a portion of channel (405) thereby overcoming the biasing force of leaf spring (430) and pivoting latch (424) such that locking body (428) pivots into a recess (422). As mentioned above, pivoting latch (424) is attached to outer tubular member (408) via pin (432), while outer tubular member (408) acts as a mechanical ground. Therefore, when locking body (428) is pivoted into a recess (422), locking body (428) may prevent trocar (402) from actuating relative to outer tuber member (408) during exemplary firing. Therefore, locking body (428) may prevent actuation of trocar (402) during exemplary firing of firing system such that gap distance d does not undesirably deviate between the operator visually confirming gap distance d and the operator stapling and severing tissue.

Once firing is complete, the operator may release trigger (74) such that trigger (74) may pivot toward the open position, causing driver actuator (410) to return the position shown in FIG. 15A, but with tissue captured between anvil (40) and staple head assembly (200) severed and stapled. With driver actuator (410) returned to the position shown in FIG. 15A, the interior surface of driver actuator (410) forcing pivoting latch (424) into engagement with recess (422) may no longer engage the end of leg (426) such that leg (426) may again rest within cutout (412). Therefore, leaf spring (430) may rotate latch (424) back to the unlocked position, thereby allowing movement of trocar (402) relative to staple head assembly (200). The operator may then rotate knob (98) with pivoting latch (424) in the unlocked position such that trocar (402) and therefore anvil (40), actuates distally thereby releasing portions of tissue (2) grasped between proximal surface (50) of anvil (40) and distally presented deck surface (222) of deck member (220).

In some embodiments, leg (426) may comprise a resilient material such that if locking body (428) is not directly aligned with one recess (422) of the array of recesses (422), contact between the interior surface of driver actuator (410) and leg (426) may flex leg (426) such that pivoting latch (424) does not inhibit the distal actuation of driver actuator (410). Therefore, if trocar (402) happens to translate during exemplary firing of staple head assembly (200), locking body (428) will engage a recess (422) once properly aligned.

FIGS. 16A-18B show an alternative handle assembly (450) that may be readily incorporated into instrument (10) in replacement of relevant portions of handle assembly (70) described above. Handle assembly (450) include a body (452), a trocar actuator (456), and a lockout feature (458); which are substantially similar to body (72), trocar actuator (231), and lockout feature (82) described above, respectively, with differences elaborated below. Lockout feature (458) is pivotably coupled to body (452) via pivot pin (459).

Handle assembly (450) may have the same components of handle assembly (70) that are not explicitly described for handle assembly (450) herein. For example, handle assembly (450) may include a trigger substantially similar to trigger (74), a trigger actuation assembly substantially similar to trigger actuation assembly (84), and an adjustment knob substantially similar to adjustment knob (98) described above. Therefore, lockout feature (458) may pivot from a locked position to an unlocked position in response to gap distance d being within a desired operating range. Further, lockout feature (458) may prevent firing of firing system when lockout feature (458) is in the locked position; while allowing firing of firing system when lockout feature (458) is in the unlocked position. As will be described in greater detail below, handle assembly (450) includes a latch assembly (460) configured to help prevent unwanted translation of a trocar actuator (456) relative to body (452) when lockout feature (458) is pivoted relative to body (452) to an unlocked position, which in turn may help prevent unwanted deviation of gap distance d as described herein.

Figure 16A:
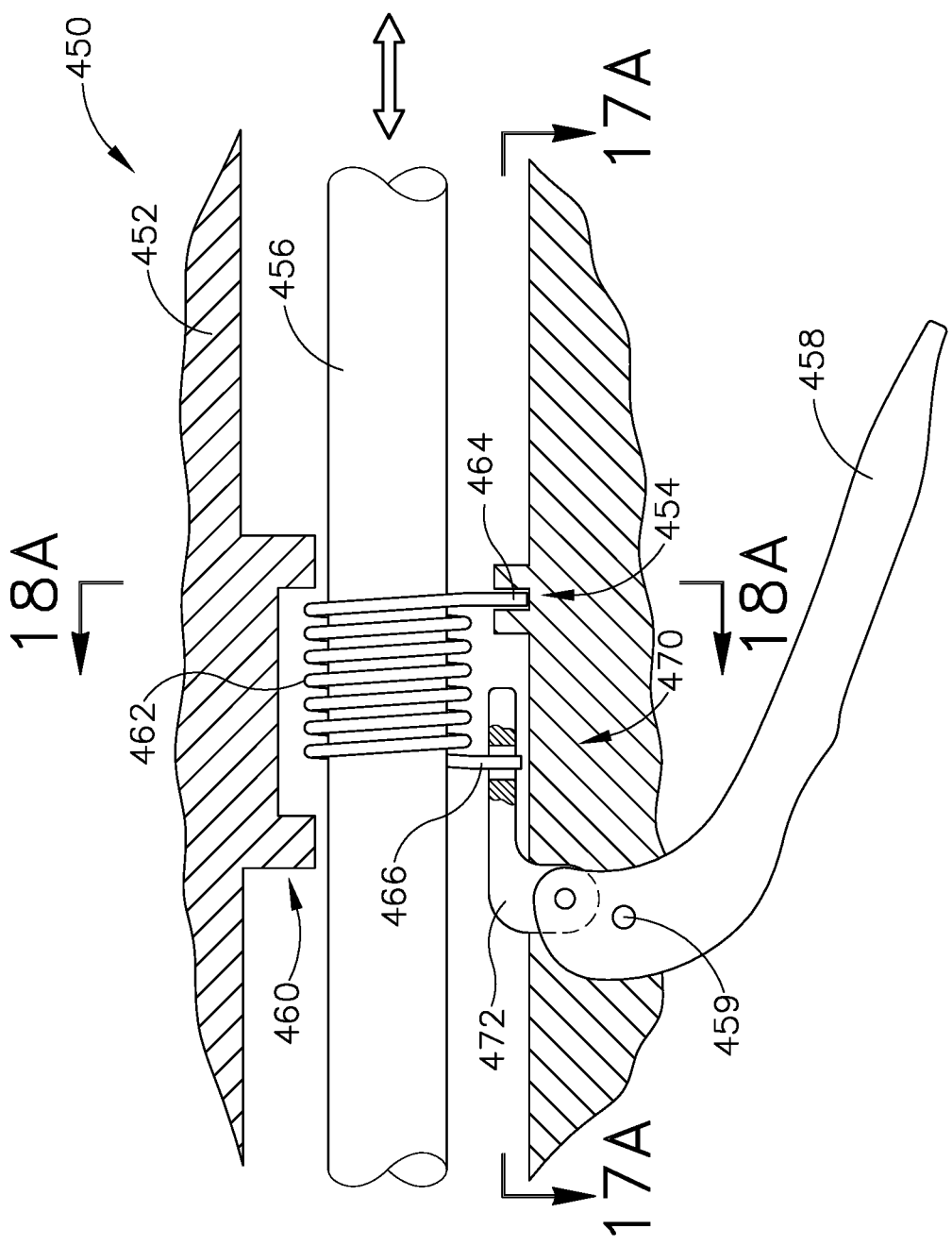
FIG. 16A depicts a cross-sectional side view of a portion of an alternative actuator handle assembly that may be readily incorporated into the surgical instrument of FIG. 1, where a lockout feature is in the locked position and a latching feature is in the unlatched position.
Figure 16B:
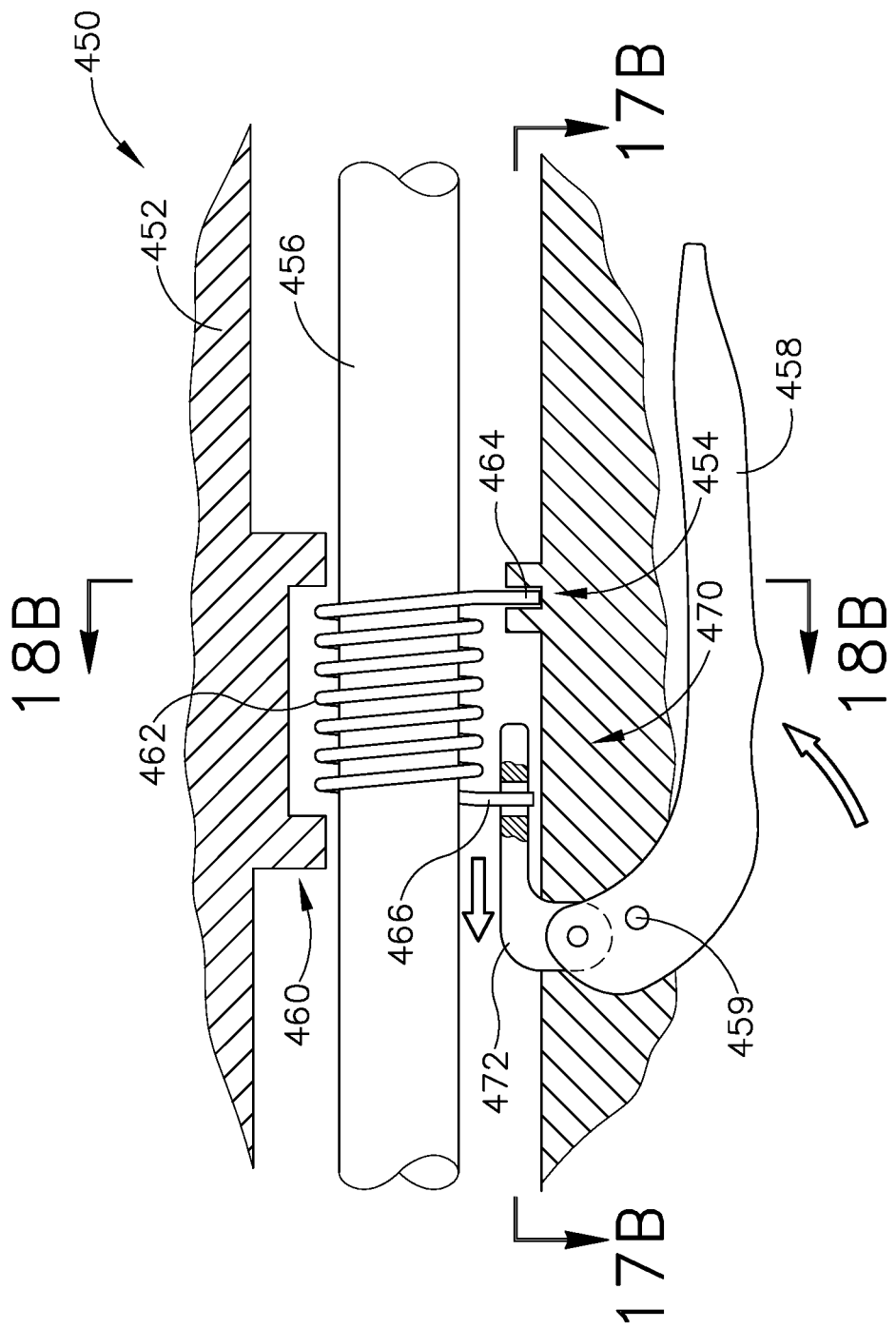
FIG. 16B depicts a cross-sectional side view of a portion of the actuator handle assembly of FIG. 16A, where the lockout feature is in an unlocked position and the latching feature is in a latched position.
Figure 18A:
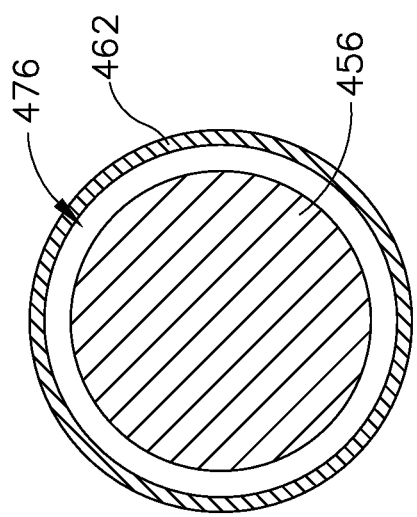
FIG. 18A depicts a cross-sectional view taken along line 18A-18A of FIG. 16A, where a torsional spring is in an unlocked position around a trocar actuator.
Figure 18B:
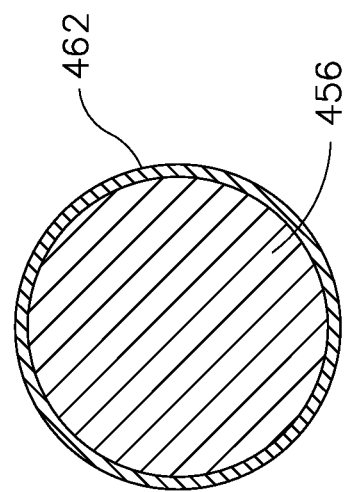
FIG. 18B depicts a cross-sectional view taken along line 18B-18B of FIG. 16B, where the torsional spring of FIG. 18A is in a locked position around the trocar actuator of FIG. 18A.

Latch assembly (460) includes a torsion spring (462) encompassing trocar actuator (456) and a camming feature (470) attached to lockout feature (458). As will be described in greater detail below, camming feature (470) is operable to actuate torsion spring (462), and therefore latch assembly (460), between an unlocked configuration (as shown in FIGS. 16A, 17A, and 18A) and a locked configuration (as shown in FIGS. 16B, 17B, and 18B) in response to lockout feature (458) pivoting between the locked position and the unlocked position. In other words, when lockout feature (458) prevents firing a firing system, latch assembly (460) may allow translation of trocar actuator (456) to suitably adjust gap distance d. Alternatively, when lockout feature (458) allows firing a firing system, latch assembly (460) may inhibit translation of trocar actuator (456) to prevent unwanted deviation a gap distance d as described above.

Torsion spring (462) includes a ground leg (464) extending from a first end of spring (462), and a moving leg (466) extending from a second end of spring (462). Ground leg (464) extends into a grounding pocket (454) defined by the interior of body (452). Therefore, ground leg (464) is effectively fixed relative to body (452). Moving leg (466) extends into an oblique slot (474) defined by a cam driver (472) of camming feature (470). As will be described in greater detail below, moving leg (466) is operable to translate laterally in response to movement of cam driver (472) in order to adjust the circumference of torsion spring (462). In particular, moving leg (466) may adjust the circumference of torsion spring (462) to selectively impart a frictional braking force on trocar actuator (456), thereby selectively inhibiting movement of trocar actuator (456).

Cam driver (472) of camming feature (470) is slidably disposed within body (452). One end of cam driver (472) is attached to lockout feature (458). As mentioned above, lockout feature (458) is configured to move from the locked position to the unlocked position when gap distance d is within a desired operating range such that firing system may be fired in accordance with the description herein. Lockout feature (458) is operable to actuate cam driver (472) from a proximal position (as shown in FIGS. 16A and 17A) to a distal position (as shown in FIGS. 16B and 17B) in response to moving from the locked position to the unlocked position.

While cam driver (472) is in the proximal position (as shown in FIGS. 16A and 17A), moving leg (466) is in a first lateral position as determined by oblique slot (474). While moving leg (466) is in the first lateral position, torsion spring (462) encompasses trocar actuator (456) to define a space (476), thereby allowing movement of trocar actuator (456). In other words, when moving leg (466) is in the first lateral position as shown in FIG. 17A, latch assembly (460) is in an unlocked configuration.

Moving lockout feature (458) from the position shown in FIG. 16A to the position shown in FIG. 16B causes distal translation of cam driver (472). Distal translation of cam driver (472) causes slot (474) of camming feature (470) to laterally actuate moving leg (466) from the first lateral position to a second lateral position (as shown in FIGS. 16B and 17B). Lateral movement of moving leg (466) causes torsion spring (462) to reduce its circumference to provide a frictional braking force against trocar actuator (456) (as shown in FIG. 18B). This frictional braking force provided by torsion spring (462) may help inhibit translation of trocar actuator (456) relative to body (452).

If the operator fires firing system in accordance with the description herein, tensile forces within trocar actuator (456) may increase. As mentioned above, this increased tensile force may lead to undesirable distal movement of trocar actuator (456), which can adversely impact gap distance d. However, since latch assembly (460) is driven into the locked configuration as described herein, the frictional braking force between spring (462) and trocar actuator (456) may prevent distal actuation of trocar actuator (456) during exemplary firing of firing system. Therefore, the gap distance d may not undesirably deviate between the operator visually confirming gap distance d and the operator stapling and severing tissue.

If the operator wishes to readjust gap distance d before or after firing, the operator may move lockout feature (458) back to the position shown in FIG. 16A such that cam driver (472) returns moving leg (466) to the first lateral position such that spring (462) and trocar actuator (456) define space (476).

Figure 19:
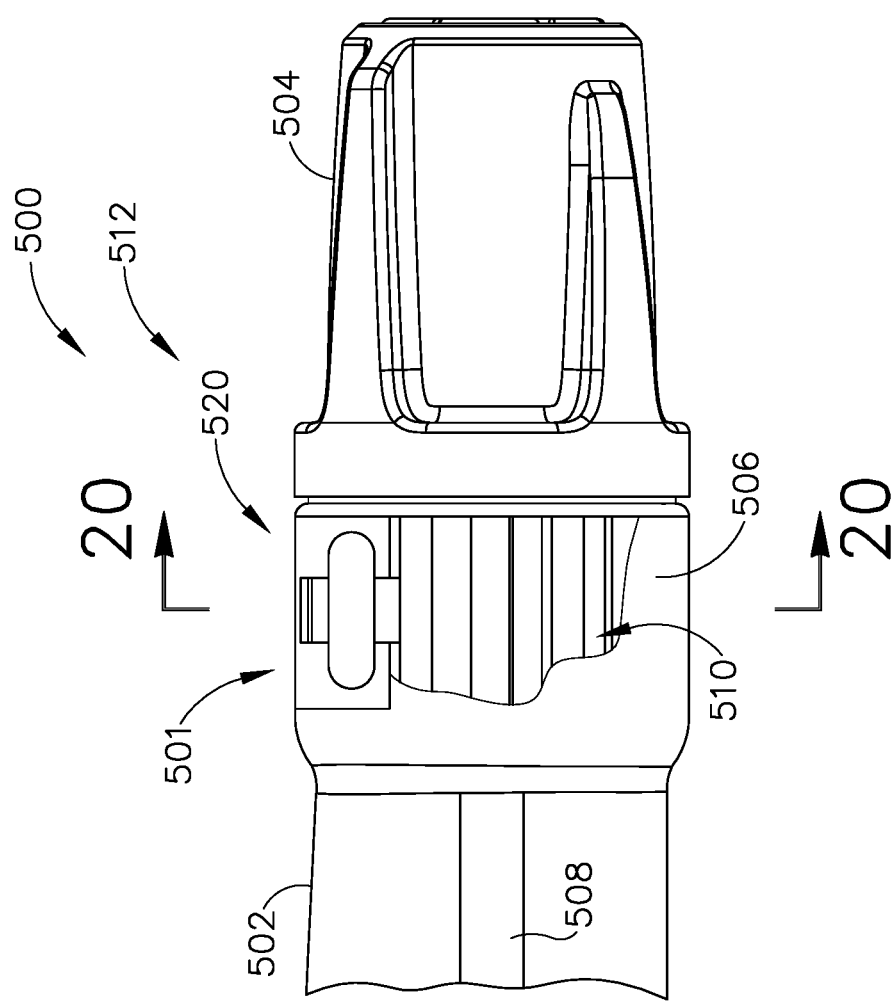
FIG. 19 depicts an elevational side view of a portion of an alternative actuator handle assembly that may be readily incorporated into the surgical instrument of FIG. 1.
Figure 20:
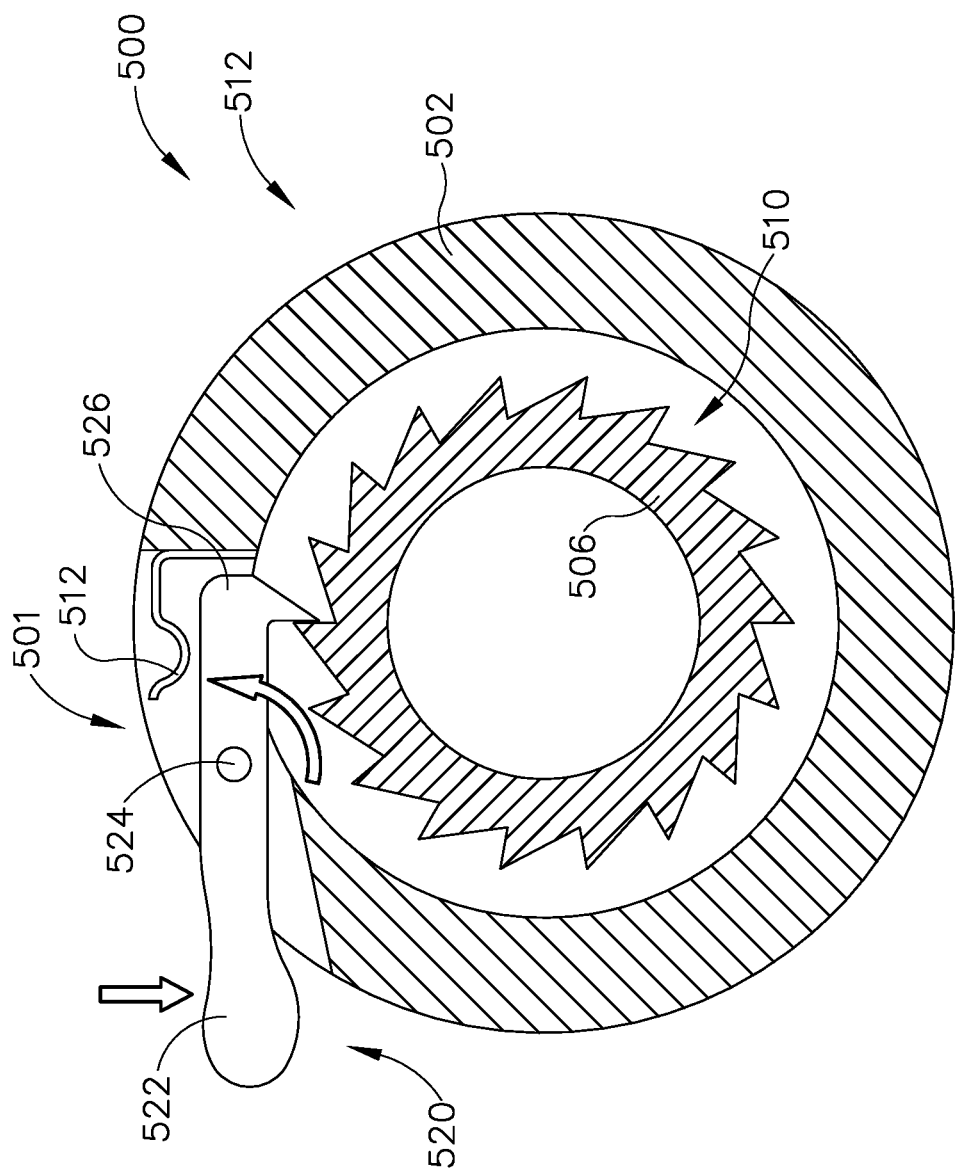
FIG. 20 depicts a cross-sectional view, taken along line 20-20 of FIG. 19, of the actuator handle assembly of FIG. 19.

FIGS. 19-20 show an alternative handle assembly (500) that may be readily incorporated into instrument (10) in replacement of relevant portions of handle assembly (70) describe above. Handle assembly (500) includes a body (502), an adjustment knob (504), a sleeve (506), and a trocar actuator (508); which are substantially similar to body (72), adjustment knob (98), sleeve (92), and trocar actuator (231) described above, respectively, with differences elaborated below. Therefore, adjustment knob (504) and sleeve (506) are configured to rotate relative to body (502) in order to translate trocar actuator (508). In particular, adjustment knob (504) and sleeve (506) may rotate in a first angular direction to actuate trocar actuator (508) proximally; while adjustment knob (504) and sleeve (506) may rotate in a second angular direction to actuate trocar actuator (508) distally.

Handle assembly (500) may have the same components of handle assembly (70) that are not explicitly described for handle assembly (500) herein. For example, handle assembly (500) may include a trigger substantially similar to trigger (74), a trigger actuation assembly substantially similar to trigger actuation assembly (84), and a lockout feature substantially similar to lockout feature (82).

As will be described in greater detail below, handle assembly (500) includes a trocar ratcheting latch assembly (512) configured to actuate between an engaged position and a disengaged position. Ratcheting latch assembly (512) is configured to help prevent unwanted distal translation of trocar actuator (508) relative to body (502) while ratcheting latch assembly (512) is in the engaged position, which in turn may help prevent unwanted deviation of gap distance d in accordance with the description herein. Additionally, ratcheting latch assembly (512) may selectively actuate from the engaged position to the disengaged position to allow distal translation of trocar actuator (508) relative to body (502).

Ratcheting latch assembly (512) includes an annular array of ratchet teeth (510) disposed on an exterior of sleeve (506), a latch lever (520) pivotably coupled with body (502) via pivot pin (524), and a leaf spring (528) attached to body (502). Latch lever (520) includes a button (522) and a pawl (526). Latch lever (520) extends through a recess (501) defined by body (502) such that button (522) extends on an exterior of body (502) and pawl (526) is directly adjacent to annular array of ratchet teeth (510). Leaf spring (528) biases latch lever (520) such that pawl (526) is engaged with annular array of ratchet teeth (510). When pawl (526) is engaged with annular array of rachet teeth (510), adjustment knob (504) and sleeve (506) are restricted to rotating in the first angular direction associated with trocar actuator (508) translating proximally. Therefore, if the operator tried to rotate adjustment knob (504) in the second angular direction while pawl (526) is engaged with annular array of rachet teeth (510), pawl (526) and teeth (510) would restrict rotation of adjustment knob (504) in the second angular direction such that trocar actuator (508) may not translate distally. If the operator desired to rotate adjustment knob (504) in the second angular direction, the operator may press down on button (522) such that pawl (526) disengaged with teeth (510). If the operator releases button (522), the bias force provided by leaf spring (528) will force pawl (526) back into engagement with teeth (510).

During exemplary use, the operator may rotate adjustment knob (504) in the first angular direction to translate trocar actuator (508) proximally while trocar (230) is suitably attached to anvil (40). The operator may rotate adjustment knob (504) to achieve a desirable gap distance d in accordance with the description above. It should be understood that spring (528) biases pawl (526) into engagement with teeth (510) such that ratcheting latch assembly (512) is in the engaged position. Therefore, latch assembly (512) prevents distal translation of trocar actuator (508).

When a desirable gap distance d is achieved, the operator may fire firing system in accordance with the description herein, thereby increasing the tensile force within trocar (230). As mentioned above, this increased tensile force may lead to undesirable distal movement of trocar actuator (508), which can adversely impact gap distance d. However, since ratcheting latch assembly (512) is in the engaged position, engagement between pawl (526) and teeth (510) helps inhibit trocar actuator (508) from actuating distally. Therefore, pawl (526) may prevent actuation of trocar actuator (508) during exemplary firing of firing system such that gap distance d does not undesirably deviate between the operator visually confirming gap distance d and the operator stapling and severing tissue. Once firing is complete, the operator may press button (522) to actuate pawl (526) in a disengaged position. The operator may then rotate knob (504) with pawl (526) in the disengaged position such that trocar acuter (508), and therefore anvil (40), actuates distally thereby releasing portions of tissue (2) grasped between proximal surface (50) of anvil (40) and distally presented deck surface (222) of deck member (220).

Figure 22:
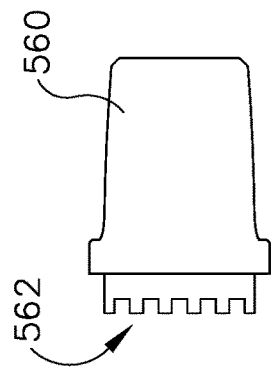
FIG. 22 depicts an elevational side view of an adjustment knob of the actuator handle assembly of FIG. 21A.
Figure 21A:
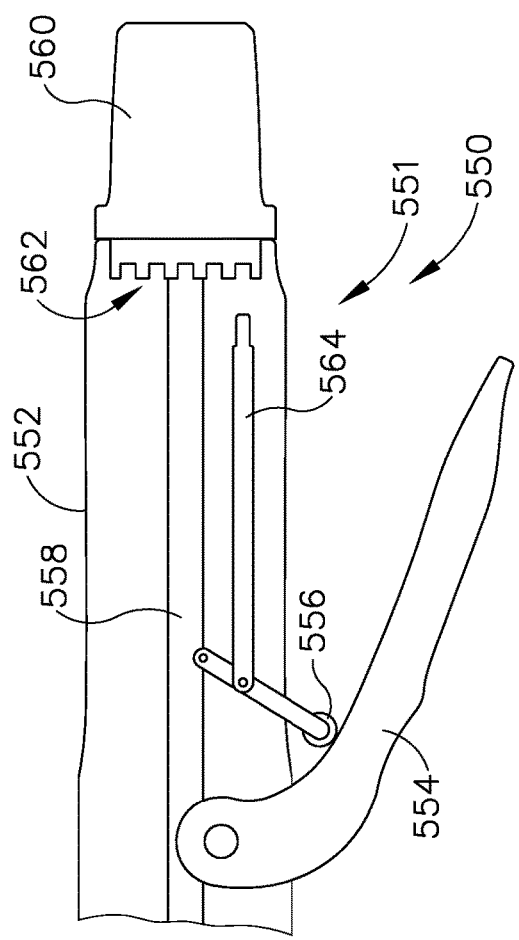
FIG. 21A depicts a cross-sectional view of an alternative actuator handle assembly that may be readily incorporated into the surgical instrument of FIG. 1, where a lockout feature is pivotably coupled with a body in a locked angular position, where a trocar latch assembly having a locking bar is in a distal unlatched position.

FIGS. 21A-22 show another alternative handle assembly (550) that may be readily incorporated into instrument (10) in replacement of relevant portions of handle assembly (70) described above. Handle assembly (550) includes a body (552), a trigger (554), a lockout feature (556), a trocar actuator (558), and an adjustment knob (560); which are substantially similar to body (72), trigger (74), lockout feature (82), trocar actuator (231), and adjustment knob (98), respectively, with difference elaborated below. Therefore, adjustment knob (560) is configured to rotate relative to body (552) in order to translate trocar actuator (558). Additionally, lockout feature (556) may pivot from a locked position to an unlocked position in response to gap distance d being within a desired operating range. Lockout feature (556) may prevent firing of firing system when lockout feature (556) is in the locked position; while lockout feature (556) may allow firing of firing system when lockout feature (556) is in the unlocked position. As will be described in greater detail below, handle assembly (550) includes a latch assembly (551) configured to help prevent unwanted translation of a trocar actuator (558) relative to body (552) when lockout feature (556) is pivoted relative to body (552) to an unlocked position, which in turn may help prevent unwanted deviation of gap distance d as described herein.

Latch assembly (551) includes a locking bar (564) slidably housed within body (552) while adjustment knob (560) includes a distal face defining an annular array of recesses (562). One end of locking bar (564) is attached to lockout feature (556) such that lockout feature (556) may actuate locking bar (564) between a distal position and a proximal position. In particular, lockout feature (556) may pivot from the locked position (as shown in FIG. 21A) to the unlocked position (as shown in FIG. 21B) in order to drive locking bar (564) from the distal position to the proximal position, respectively.

As best seen in FIG. 21A, in the distal position, a proximal end of locking bar (564) is disengaged with annular array of recesses (562), thereby allowing rotation of adjustment knob (504) and translation of trocar actuator (558). Therefore, when lockout feature (556) prevents firing a firing system (as shown in FIG. 21A), latch assembly (551) may allow translation of trocar actuator (558) to suitably adjust gap distance d.

Figure 21B:
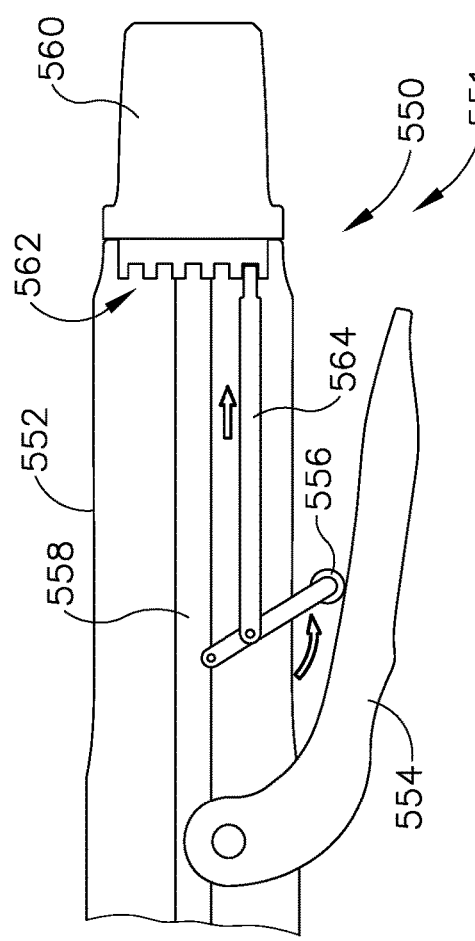
FIG. 21B depicts a cross-sectional view of the actuator handle assembly of FIG. 21A, where the lockout feature is pivotably coupled with the body in an unlocked angular position, where the locking bar of the trocar latch assembly is in a proximal latched position.

As best seen in FIG. 21B, in the proximal position, a proximal end of locking bar (564) is configured to engage a recess (562) of the annular array of recesses (562), thereby rotationally locking adjustment knob (504) relative to body (552). With adjustment knob (504) rotationally locked relative to body (552), trocar actuator (558) is longitudinally fixed relative to body (552). Therefore, when lockout feature (556) allows firing a firing system (as shown in FIG. 21B), latch assembly (551) may inhibit translation of trocar actuator (558) to prevent unwanted deviation of gap distance d as described herein. If the operator fires firing system in accordance with the description herein, tensile forces within trocar actuator (558) may increase. As mentioned above, this increased tensile force may lead to undesirable distal movement of trocar actuator (558), which can adversely impact gap distance d. However, since locking bar (564) is engaged with adjustment knob (504) as described herein, the rotational locking of adjustment knob (504) helps prevent distal actuation of trocar actuator (558) during exemplary firing of firing system. Therefore, the gap distance d may not undesirably deviate between the operator visually confirming gap distance d and the operator stapling and severing tissue.

If the operator wishes to readjust gap distance d before or after firing, the operator may move lockout feature (556) back to the position shown in FIG. 21A such that locking bar (564) returns to the distal position.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a handle assembly comprising a body; (b) a shaft assembly comprising an outer tubular member extending distally from the body; (c) an end effector comprising: (i) a staple deck fixed relative to the outer tubular member, (ii) a staple driver, wherein the staple driver is operable to actuate relative to the staple deck between an unfired position and a fired position, and (iii) a trocar configured to actuate relative to the staple deck and the staple driver; (d) an anvil configured to selectively couple with the trocar, wherein the trocar is operable to actuate the anvil relative to the staple deck to define a gap distance; and (e) a trocar latch assembly comprising a locking body configured to actuate between an unlocked configuration and a locked configuration in response to the staple driver actuating between the unfired position and the fired position, wherein the locking body is configured to selectively fix the trocar relative to the staple deck in the locked configuration.

Example 2

The apparatus of Example 1, wherein the locking body is slidably coupled with the housing.

Example 3

The apparatus of any one or more of Examples 1 through 2, wherein the handle assembly further comprises a trocar actuator coupled with the trocar, wherein the trocar latch assembly further comprises an array of locking teeth extending along the trocar actuator.

Example 4

The apparatus of Example 3, wherein the locking body is configured to mesh with the array of locking teeth in the locked configuration.

Example 5

The apparatus of any one or more of Examples 1 through 4, wherein the handle assembly further comprises a trigger configured to actuate the staple driver between the unfired position and the fired position.

Example 6

The apparatus of Example 5, wherein the locking body is coupled to the trigger via a spring.

Example 7

The apparatus of any one or more of Examples 1 through 6, wherein the locking body is pivotably coupled to the outer tubular member.

Example 8

The apparatus of any one or more of Examples 1 through 7, wherein the trocar latch further comprises a biasing member that biases the locking body toward the unlocked configuration.

Example 9

The apparatus of Example 8, wherein the shaft assembly further comprises a driver actuator coupled to the staple driver, wherein the driver actuator is configured to pivot the locking body toward the locked configuration in response to the staple driver actuating from the unfired position to the fired position.

Example 10

The apparatus of Example 9, wherein the trocar defines an array of recesses configured to couple with the locking body in the locked configuration.

Example 11

The apparatus of Example 10, wherein the locking body further comprises a resilient leg.

Example 12

The apparatus of any one or more of Examples 1 through 11, wherein the handle assembly further comprises an adjustable knob configured to rotate relative to the body in order to actuate the trocar relative to the staple deck.

Example 13

The apparatus of any one or more of Examples 1 through 12, further comprising a staple driver lockout configured to prevent the staple driver from actuating between the unfired position and the fired position unless the gap distance is within a predetermined range.

Example 14

The apparatus of any one or more of Examples 1 through 13, wherein the staple driver lockout is pivotably coupled with the body.

Example 15

An apparatus, comprising: (a) a handle assembly comprising a body; (b) a shaft assembly comprising an outer tubular member extending distally from the body; (c) an end effector comprising: (i) a staple deck fixed relative to the outer tubular member, (ii) a staple driver, wherein the staple driver is operable to actuate relative to the staple deck between an unfired position and a fired position, and (iii) a trocar configured to actuate relative to the staple deck and the staple driver; (d) an anvil configured to selectively couple with the trocar, wherein the trocar is operable to actuate the anvil relative to the staple deck to define a gap distance; and (e) a trocar latch assembly comprising a locking body configured actuate between an unlocked configuration and a locked configuration, wherein the locking body is configured to selectively prevent distal actuation of the trocar relative to the staple deck in the locked configuration, wherein the locking body is biased toward the locked configuration.

Example 16

The apparatus of Example 15, wherein the locking body further comprises a ratchet pawl.

Example 17

The apparatus of Example 16, wherein the locking body is pivotably coupled to the body.

Example 18

The apparatus of Example 17, wherein the handle assembly further comprises a trocar actuator attached to the trocar, wherein the trocar actuator comprises a series of ratchet teeth configured to mesh with the ratchet pawl in the locked configuration.

Example 19

The apparatus of Example 16, wherein the handle assembly further comprises an adjustable knob configured to rotate relative to the body in order to actuate the trocar, wherein the adjustable knob comprises an annular array of ratchet teeth configured to mesh with ratchet pawl.

Example 20

An apparatus, comprising: (a) an end effector comprising: (i) a staple deck fixed relative to the outer tubular member, (ii) a staple driver, wherein the staple driver is operable to actuate relative to the staple deck between an unfired position and a fired position, and (iii) a trocar configured to actuate relative to the staple deck and the staple driver; (b) an anvil configured to selectively couple with the trocar, wherein the trocar is operable to actuate the anvil relative to the staple deck to define a gap distance; and (c) a trocar latch assembly comprising a locking body configured actuate between an unlocked configuration and a locked configuration, wherein the locking body is configured to prevent distal actuation of the trocar relative to the staple deck in the locked configuration, wherein the locking body is configured to allow proximal actuation of the trocar relative to the staple deck in the locked configuration, a wherein the locking body is biased toward the locked configuration.

IV. Miscellaneous

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 16/159,851, entitled "Dual Stage Closure System for Circular Surgical Stapler," filed on Oct. 15, 2018, published as U.S. Pub. No. 2020/0113566 on Apr. 16, 2020; and U.S. application Ser. No. 16/159,854, entitled "Dual Lever to Reduce Force to Fire in Circular Surgical Stapler," filed on Oct. 15, 2018, published as U.S. Pub. No. 2020/0113567. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a handle assembly comprising a body and a trigger;
   (b) a shaft assembly comprising an outer tubular member extending distally from the body;
   (c) an end effector comprising:
      (i) a staple deck fixed relative to the outer tubular member,
      (ii) a staple driver, wherein the staple driver is operable to actuate relative to the staple deck between an unfired position and a fired position, wherein the trigger is operable to actuate the staple driver between the unfired position and the fired position, and
      (iii) an elongated coupling member configured to actuate relative to the staple deck and the staple driver;
   (d) an anvil configured to selectively couple with the elongated coupling member, wherein the elongated coupling member is operable to actuate the anvil relative to the staple deck to define a gap distance; and
   (e) a latch assembly comprising a locking body and a resilient member configured to actuate the locking body, wherein the locking body is configured to actuate between an unlocked configuration and a locked configuration in response to the staple driver actuating between the unfired position and the fired position, wherein the locking body is configured to selectively fix the elongated coupling member relative to the staple deck in the locked configuration, wherein the resilient member is in direct engagement with both the trigger and the locking body such that a position of the locking body is dependent on a position of the trigger.

2. The apparatus of claim 1, wherein the locking body is slidably coupled with the body.

3. The apparatus of claim 2, wherein the handle assembly further comprises an actuator coupled with the elongated coupling member, wherein the latch assembly further comprises an array of locking teeth extending along the actuator.

4. The apparatus of claim 3, wherein the locking body is configured to mesh with the array of locking teeth in the locked configuration.

5. The apparatus of claim 1 wherein the handle assembly further comprises an adjustable knob configured to rotate relative to the body in order to actuate the elongated coupling member relative to the staple deck.

6. The apparatus of claim 1, further comprising a staple driver lockout configured to prevent the staple driver from actuating between the unfired position and the fired position unless the gap distance is within a predetermined range.

7. The apparatus of claim 6, wherein the staple driver lockout is pivotably coupled with the body.

8. The apparatus of claim 1, wherein the resilient member comprises a spring comprising a first leg coupled to the trigger.

9. The apparatus of claim 8, wherein the spring comprises a second leg coupled to the locking body.

10. The apparatus of claim 1, wherein the elongated coupling member comprises a trocar.

11. The apparatus of claim 1, wherein the resilient member is coupled to a rod of the handle assembly.

12. An apparatus, comprising:
(a) a body;
(b) a trigger configured to actuate relative to the body;
(c) a shaft assembly comprising an outer tubular member extending distally from the body;
(d) an end effector comprising:
   (i) a staple deck fixed relative to the outer tubular member,
   (ii) a staple driver, wherein the staple driver is operable to actuate relative to the staple deck between an unfired position and a fired position, wherein the trigger is operable to actuate the staple driver between the unfired position and the fired position, and
   (iii) an elongated coupling member configured to actuate relative to the staple deck and the staple driver;
(e) an anvil configured to selectively couple with the elongated coupling member, wherein the elongated coupling member is operable to actuate the anvil relative to the staple deck to define a gap distance; and
(f) a latch assembly comprising a locking body and a biasing member, wherein the biasing member is coupled to both the locking body and the trigger, wherein the latch assembly is configured to actuate relative to the trigger between an unlocked configuration and a locked configuration, wherein the latch assembly is configured to inhibit movement of the elongated coupling member relative to the staple deck in the locked configuration, wherein the latch assembly is configured to permit movement of the elongated coupling member relative to the staple deck in the unlocked configuration, wherein the trigger is operable to drive the latch assembly toward the locked configuration while actuating the staple driver from the unfired position toward the fired position.

13. The apparatus of claim 12, wherein the latch assembly comprises a latch body and a spring, wherein the spring connects the trigger with the latch body.

14. The apparatus of claim 13, wherein the latch body is slidably contained within the body.

15. An apparatus, comprising:
(a) a body;
(b) a trigger configured to actuate relative to the body;
(c) a shaft assembly comprising an outer tubular member extending distally from the body;
(d) an end effector comprising:
   (i) a staple deck fixed relative to the outer tubular member,
   (ii) a staple driver, wherein the staple driver is operable to actuate relative to the staple deck between an unfired position and a fired position, wherein the trigger is operable to actuate the staple driver between the unfired position and the fired position, and
   (iii) an elongated coupling member configured to actuate relative to the staple deck and the staple driver;
(e) an anvil, wherein the elongated coupling member is operable to actuate the anvil relative to the staple deck to define a gap distance; and
(f) a latch assembly configured to actuate relative to the trigger from an unlocked configuration toward a locked configuration in direct response to the trigger actuating relative to the body, wherein the latch assembly is configured to inhibit movement of the elongated coupling member relative to the staple deck in the locked configuration while the staple driver is being driven into the fired position.

* * * * *